United States Patent
Kondoh et al.

(10) Patent No.: US 7,860,547 B2
(45) Date of Patent: Dec. 28, 2010

(54) VISCERAL FAT MEASURING APPARATUS, VISCERAL FAT MEASURING METHOD, PROGRAM, AND RECORDING MEDIUM

(75) Inventors: Kazuya Kondoh, Osaka (JP); Shinji Uchida, Osaka (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 1765 days.

(21) Appl. No.: 10/512,718

(22) PCT Filed: Feb. 17, 2004

(86) PCT No.: PCT/JP2004/001710

§ 371 (c)(1),
(2), (4) Date: Oct. 27, 2004

(87) PCT Pub. No.: WO2004/073517

PCT Pub. Date: Sep. 2, 2004

(65) Prior Publication Data

US 2005/0197575 A1    Sep. 8, 2005

(30) Foreign Application Priority Data

Feb. 18, 2003    (JP) .............................. 2003-039916

(51) Int. Cl.
*A61B 5/05*    (2006.01)
(52) U.S. Cl. ......................... 600/407; 600/547; 128/920
(58) Field of Classification Search .................. 600/547, 600/587, 309–310, 607, 476, 437, 438; 128/920
See application file for complete search history.

(56) References Cited

U.S. PATENT DOCUMENTS 5,156,161 A    10/1992    Lollar 6,487,445 B1 *    11/2002    Serita et al. .................. 600/547
6,530,886 B1 *    3/2003    Ishida et al. .................. 600/442

(Continued)

FOREIGN PATENT DOCUMENTS

EP    0942260 A1    9/1999

(Continued)

OTHER PUBLICATIONS

International Search Report for PCT/JP2004/001710, dated May 25, 2004, (with English translation).

(Continued)

*Primary Examiner*—Brian Casler
*Assistant Examiner*—Nasir Shahrestani
(74) *Attorney, Agent, or Firm*—RatnerPrestia

(57) ABSTRACT

A subcutaneous fat measuring unit measures the subcutaneous fat thickness by pressing a predetermined face against the living body surface. A pressing pressure measuring unit measures the pressure applied from the subcutaneous fat measuring unit to the living body surface, and a database holds information on the relationship among the values of a plurality of subcutaneous fat thicknesses in the condition where no pressure is applied to the living body surface, the pressure applied to the living body surface with respect to each of the plurality of subcutaneous fat thicknesses and the subcutaneous fat thickness in a condition where the pressure is applied. A calculating unit calculates the subcutaneous fat thickness in a condition where no pressure is applied to the living body surface, by use of the database based on the subcutaneous fat thickness measured by the subcutaneous fat measuring unit and the pressure applied to the living body surface which pressure is measured by the pressing pressure measuring unit. And a visceral fat calculating unit calculates the amount of visceral fat from the calculated subcutaneous fat thickness.

10 Claims, 18 Drawing Sheets

U.S. PATENT DOCUMENTS

| | | | |
|---|---|---|---|
| 2002/0123695 A1* | 9/2002 | Kawanishi | 600/547 |
| 2003/0158501 A1* | 8/2003 | Uchida et al. | 600/587 |
| 2004/0102684 A1 | 5/2004 | Kawanishi et al. | |
| 2004/0152962 A1 | 8/2004 | Kondoh et al. | |

FOREIGN PATENT DOCUMENTS

| | | | |
|---|---|---|---|
| EP | 1 344 490 A1 | | 9/2003 |
| EP | 1 396 227 A1 | | 3/2004 |
| JP | 60-181606 A | | 9/1985 |
| JP | 04-034409 B2 | | 6/1992 |
| JP | 10-314145 | | 12/1998 |
| JP | 2953909 | | 7/1999 |
| JP | 3035791 | | 2/2000 |
| JP | 2000-350710 A | | 12/2000 |
| JP | 2001-212111 A1 | | 8/2001 |
| JP | 2003-310575 A | | 11/2003 |
| WO | WO 01/76485 A1 | | 10/2001 |
| WO | WO 01/78600 A1 | | 10/2001 |
| WO | WO 0176485 A1 | * | 10/2001 |
| WO | WO 02/051309 A1 | | 7/2002 |
| WO | WO 03/063704 A1 | | 8/2003 |

OTHER PUBLICATIONS

Yuji Matsuzawa, et al., "Atarashii himan no hantei to himansho no shindan kijun (new obesity determination and obesity diagnosis criteria)", Himan Kenkyu (obesity research), vol. 6, No. 1, 2000 <Committee Report> Obesity Diagnosis Criteria Examination Committee of the Japan Society for the Study of Obesity, with partial English translation.

Supplementary European Search Report for Application No. EP 04 71 1760, Jan. 25, 2010, Panasonic Corporation.

* cited by examiner

VISCERAL FAT MEASURING APPARATUS, VISCERAL FAT MEASURING METHOD, PROGRAM, AND RECORDING MEDIUM

This Application is a U.S. National Phase Application of PCT International Application PCT/W2004/001710.

TECHNICAL FIELD

The present invention relates to a visceral fat measuring apparatus, a visceral fat measuring method, a program, and a recording medium of measuring information about the visceral fat.

BACKGROUND ART

Conventionally, as methods of measuring subcutaneous fat thickness, the following are known: a method using ultrasonic waves (see, for example, Japanese Patent No. 2953909); a method using near infrared rays (see, for example, Japanese Patent No. 3035791); and a method using a caliper (see, for example, Japanese Laid-Open Patent Application No. H10-314145). Moreover, it has been reported that the visceral fat area is highly correlated with a waist girth (see, for example, Yuji MATSUZAWA and 13 others, "Atarashii himan no hantei to himansho no shindan kijun (new obesity determination and obesity diagnosis criteria), *Himan Kenkyu* (obesity research), Vol. 6, No. 1, 2000 <Committee Report> Obesity Diagnosis Criteria Examination Committee of the Japan Society for the Study of Obesity).

The disclosure of Japanese Patent No. 2953909, Japanese Patent No. 3035791, and "Yuji MATSUZAWA and 13 others, "Atarashii himan no hantei to himansho no shindan kijun (new obesity determination and obesity diagnosis criteria), *Himan Kenkyu* (obesity research), Vol. 6, No. 1, 2000 <Committee Report> Obesity Diagnosis Criteria Examination Committee of the Japan Society for the Study of Obesity" are incorporated herein by reference in their entireties.

However, according to a conventional method using ultrasonic waves or near infrared rays, since measurement is performed by bringing ultrasonic waves or near infrared rays into contact with a measurement part, subcutaneous fat which is soft becomes deformed. Variations in the condition of a contact with a measurement part make the measured subcutaneous fat thickness unstable, thereby degrading measurement repeatability. In addition, since the subcutaneous fat becomes deformed, the obtained subcutaneous fat thickness is different from the value in the natural state in which no force is applied to the measurement part. On the other hand, according to the method using a caliper, it is difficult to accurately determine the measurement place. In addition, since the manner in which a skin is pulled and the measurement method vary among measurers, the measurement value varies.

With respect to a waist girth which has been reported to be highly correlated with a visceral fat area, since the ratio between subcutaneous fat and visceral fat differs among persons (in particular, between men and women), there is no difference in waist girth between persons who are thick in subcutaneous fat and small in the amount of visceral fat and persons who are thin in subcutaneous fat and large in the amount of visceral fat although there is a difference in visceral fat area. That is, a waist girth is an information amount not considering the influence of subcutaneous fat although correlated with a visceral fat amount. Moreover, when a tape measure is used to measure a waist girth, the measurement repeatability of the waist girth is inferior because the strength of pulling of the tape measure varies among measurers.

DISCLOSURE OF INVENTION

Accordingly, in view of the above-mentioned conventional problems, an object of the present invention is to provide a visceral fat measuring apparatus, a visceral fat measuring method, a program and a recording medium being excellent in measurement repeatability and capable of accurately measuring information correlated with a visceral fat amount from subcutaneous fat thickness by measuring subcutaneous fat thickness in the condition where no pressure is applied to a measurement part.

Another object of the present invention is to provide a visceral fat measuring apparatus, a visceral fat measuring method, a program and a recording medium capable of measuring an information amount correlated with a visceral fat amount which information amount does not include the influence of the subcutaneous fat.

A first aspect of the invention is a visceral fat measuring apparatus comprising:
  a subcutaneous fat measuring unit of measuring a subcutaneous fat thickness by pressing a predetermined face against a living body surface;
  a calculating unit of calculating a subcutaneous fat thickness in a condition where no pressure is applied to the living body surface, based on the subcutaneous fat thickness measured by said subcutaneous fat measuring unit; and
  a visceral fat calculating unit of calculating an information amount correlated with a visceral fat amount from the calculated subcutaneous fat thickness.

Moreover, a second aspect of the invention is the visceral fat measuring apparatus according to the first aspect of the invention, comprising: a pressing pressure measuring unit of measuring a pressure applied from said subcutaneous fat measuring unit to the living body surface; and
  a database of holding information on a relationship among values of a plurality of subcutaneous fat thicknesses in the condition where no pressure is applied to the living body surface, a pressure applied to the living body surface with respect to each of the plurality of subcutaneous fat thicknesses and a subcutaneous fat thickness in a condition where the pressure is applied,
  wherein said calculating unit calculates the subcutaneous fat thickness in the condition where no pressure is applied to the living body surface, by use of said database based on the subcutaneous fat thickness measured by said subcutaneous fat measuring unit and the pressure applied to the living body surface which pressure is measured by said pressing pressure measuring unit.

Moreover, a third aspect of the invention is the visceral fat measuring apparatus according to the first aspect of the invention, comprising a database of holding information on a relationship between values of a plurality of subcutaneous fat thicknesses in the condition where no pressure is applied to the living body and a subcutaneous fat thickness in a condition where a pressure of not less than a predetermined pressure value is applied to the living body surface with respect to each of the plurality of subcutaneous fat thicknesses,
  wherein said subcutaneous fat measuring unit measures the subcutaneous fat thickness by pressing the predetermined face against the living body surface at a pressure of not less than the predetermined pressure value, and
  wherein said calculating unit calculates the subcutaneous fat thickness in the condition where no pressure is applied to the living body surface, by use of said database based on the subcutaneous fat thickness measured by said subcutaneous fat measuring unit.

Moreover, the fourth aspect of the invention is the visceral fat measuring apparatus according to the first aspect of the invention, wherein said information amount correlated with the visceral fat amount is an amount of visceral fat, and wherein said visceral fat calculating unit calculates the amount of visceral fat by use of an expression 1 from the calculated subcutaneous fat thickness:

$$S=D_0 \times T_0 + E_0 \qquad \text{(Expression 1)}$$

where S is the amount of visceral fat, $T_0$ is the calculated subcutaneous fat thickness in the condition where no pressing pressure is applied to said living body surface, and $D_0$ and $E_0$ are predetermined constants.

Moreover, a fifth aspect of the invention is a visceral fat measuring apparatus comprising:

a subcutaneous fat measuring unit of measuring a subcutaneous fat thickness by pressing a predetermined face against a living body surface;

a pressing pressure measuring unit of measuring a pressure applied from the subcutaneous fat measuring unit to the living body surface; and a visceral fat calculating unit of calculating an amount of visceral fat by use of an expression 2 based on the subcutaneous fat thickness measured by said subcutaneous fat measuring unit and the pressure applied to the living body surface which pressure is measured by said pressing pressure measuring unit:

$$S=D \times ((T-Be^{-CF})/(A-1)e^{-CF}+1))+E \qquad \text{(Expression 2)}$$

where S is the amount of visceral fat,

F is the pressure applied to the living body surface which pressure is measured by said pressing pressure measuring unit, T is the subcutaneous fat thickness measured by said subcutaneous fat measuring unit, A, B, C, D and E are predetermined constants, and e is a base of a natural logarithm.

Moreover, a sixth aspect of the invention is a visceral fat measuring apparatus comprising: a subcutaneous fat measuring unit of measuring a subcutaneous fat thickness by pressing a predetermined face against a living body surface at a pressure of not less than a predetermined pressure value; and a visceral fat calculating unit of calculating an amount of visceral fat by use of an expression 3 based on the subcutaneous fat thickness measured by said subcutaneous fat measuring unit:

$$S=D \times T_\infty + E \qquad \text{(Expression 3)}$$

where S is the amount of visceral fat, $T_\infty$ is the subcutaneous fat thickness measured by said subcutaneous fat measuring unit, and D and E are predetermined constants.

Moreover, a seventh aspect of the invention is the visceral fat measuring apparatus according to the first aspect of the invention, wherein said information amount correlated with the visceral fat amount is an amount of visceral fat, wherein said visceral fat calculating unit has an abdominal girth inputting unit of inputting an abdominal girth, and wherein the amount of visceral fat is calculated by use of an expression 4 from the calculated subcutaneous fat thickness:

$$S=G_0 \times L - H_0 \times T_0 + I_0 \qquad \text{(Expression 4)}$$

where S is the amount of visceral fat, $T_0$ is the calculated subcutaneous fat thickness in the condition where no pressing pressure is applied to said living body surface, L is said abdominal girth, and $G_0$, $H_0$ and $I_0$ are predetermined constants.

Moreover, an eighth aspect of the invention is a visceral fat measuring apparatus comprising: a subcutaneous fat measuring unit of measuring a subcutaneous fat thickness by pressing a predetermined face against a living body surface;

a pressing pressure measuring unit of measuring a pressure applied from said subcutaneous fat measuring unit to the living body surface; and a visceral fat calculating unit of having an abdominal girth inputting unit of inputting an abdominal girth, and calculating an amount of visceral fat by use of an expression 5 based on the subcutaneous fat thickness measured by said subcutaneous fat measuring unit and the pressure applied to said living body surface which pressure is measured by said pressing pressure measuring unit:

$$S=G \times L - H \times (T-Be^{-CF})/((A-1)e^{-CF}+1))+I \qquad \text{(Expression 5)}$$

where S is said amount of visceral fat,

F is the pressure applied to said living body surface which pressure is measured by said pressing pressure measuring unit, T is the subcutaneous fat thickness measured by said subcutaneous fat measuring unit, L is said abdominal girth, A, B, C, D, E, G, H and I are predetermined constants, and e is a base of a natural logarithm.

Moreover, a ninth aspect of the invention is a visceral fat measuring apparatus comprising: a subcutaneous fat measuring unit of measuring a subcutaneous fat thickness by pressing a predetermined face against a living body surface at a pressure of not less than a predetermined pressure value; and a visceral fat calculating unit of having an abdominal girth inputting unit of inputting an abdominal girth, and calculating an amount of visceral fat by use of an expression 6 based on the subcutaneous fat thickness measured by said subcutaneous fat measuring unit:

$$S=G \times L - H \times T_\infty + I \qquad \text{(Expression 6)}$$

where S is said amount of visceral fat, $T_\infty$ is the subcutaneous fat thickness measured by said subcutaneous fat measuring unit, L is said abdominal girth, and G, H and I are predetermined constants.

Moreover, a tenth aspect of the invention is the visceral fat measuring apparatus according to the third or the sixth aspect of the invention, wherein said predetermined pressure value is not less than 10000 Pa.

Moreover, an eleventh aspect of the invention is the visceral fat measuring apparatus according to any one of the first to the ninth aspects of the invention, wherein said subcutaneous fat measuring unit is an optical subcutaneous fat measuring apparatus.

Moreover, a twelfth aspect of the invention is the visceral fat measuring apparatus according to any one of the first to the ninth aspects of the invention, wherein said subcutaneous fat measuring unit is an ultrasonic measuring apparatus.

Moreover, a thirteenth aspect of the invention is the visceral fat measuring apparatus according to the twelfth aspect of the invention, wherein said subcutaneous fat measuring unit comprises:

an ultrasonic element of measuring the subcutaneous fat thickness by use of a reflected wave;

a domical lid of forming an enclosed space between said ultrasonic element and said living body surface; and a soft body of being filled in the space.

Moreover, a fourteenth aspect of the invention is the visceral fat measuring apparatus according to any one of the seventh to the ninth aspects of the invention, comprising an abdominal girth measuring unit of measuring the abdominal girth, wherein said abdominal girth inputting unit inputs the measured abdominal girth.

Moreover, an fifteenth aspect of the invention is the visceral fat measuring apparatus according to the fourteenth aspect of the invention, wherein said abdominal girth measuring unit comprises:

a string;

a reel of winding up said string; and a counter of counting the number of rotations of said reel.

Moreover, a sixteenth aspect of the invention is the visceral fat measuring apparatus according to the fifteenth aspect of the invention, wherein said abdominal girth calculating unit comprises a tension adjusting mechanism of holding a tension of said string at a predetermined value.

Moreover, a seventeenth aspect of the invention is the visceral fat measuring apparatus according to any one of the first to the ninth aspects of the invention, comprising a fixing unit of fixing said subcutaneous fat measuring unit in a predetermined position on said living body surface.

Moreover, an eighteenth aspect of the invention is the visceral fat measuring apparatus according to the seventeenth aspect of the invention, wherein said fixing unit has a protrusion of being inserted into a navel.

Moreover, an nineteenth aspect of the invention is a visceral fat measuring method comprising: a subcutaneous fat measurement step of measuring a subcutaneous fat thickness by pressing a predetermined face against a living body surface;

a calculation step of calculating a subcutaneous fat thickness in a condition where no pressure is applied to the living body surface, based on the subcutaneous fat thickness measured by said subcutaneous fat measuring step; and a visceral fat calculation step of calculating an information amount correlated with a visceral fat amount from the calculated subcutaneous fat thickness.

Moreover, a twentieth aspect of the invention is a visceral fat measuring method comprising: a subcutaneous fat measurement step of measuring a subcutaneous fat thickness by pressing a predetermined face against a living body surface;

a pressing pressure measurement step of measuring a pressure applied from said subcutaneous fat measuring step to said living body surface; and a visceral fat calculation step of calculating an amount of visceral fat by use of an expression 2 based on the subcutaneous fat thickness measured by said subcutaneous fat measuring step and the pressure applied to said living body surface which pressure is measured by said pressing pressure measuring step:

$$S = D \times ((T - Be^{-CF})/(A-1)e^{-CF} + 1)) + E \qquad \text{(Expression 2)}$$

where S is said amount of visceral fat,

F is the pressure applied to said living body surface which pressure is measured by said pressing pressure measuring step, T is the subcutaneous fat thickness measured by said subcutaneous fat measuring step, A, B, C, D and E are predetermined constants, and e is a base of a natural logarithm.

Moreover, a twenty-first aspect of the invention is a visceral fat measuring method comprising: a subcutaneous fat measuring step of measuring a subcutaneous fat thickness by pressing a predetermined face against a living body surface at a pressure of not less than a predetermined pressure value; and a visceral fat calculation step of calculating an amount of visceral fat by use of an expression 3 based on the subcutaneous fat thickness measured by said subcutaneous fat measuring step:

$$S = D \times T_\infty + E \qquad \text{(Expression 3)}$$

where S is said amount of visceral fat, $T_\infty$ is the subcutaneous fat thickness measured by said subcutaneous fat measuring step, and D and E are predetermined constants.

A twenty-second aspect of the invention is a visceral fat measuring method comprising: a subcutaneous fat measurement step of measuring a subcutaneous fat thickness by pressing a predetermined face against a living body surface;

a pressing pressure measurement step of measuring a pressure applied from said subcutaneous fat measuring step to said living body surface; and a visceral fat calculation step of having an abdominal girth inputting step of inputting an abdominal girth, and calculating an amount of visceral fat by use of an expression 5 based on the subcutaneous fat thickness measured by said subcutaneous fat measuring step and the pressure applied to said living body surface which pressure is measured by said pressing pressure measuring step:

$$S = G \times L - H \times (T - Be^{-CF})/((A-1)e^{-CF} + 1)) + I \qquad \text{(Expression 5)}$$

where S is said amount of visceral fat,

F is the pressure applied to said living body surface which pressure is measured by said pressing pressure measuring step, T is the subcutaneous fat thickness measured by said subcutaneous fat measuring step, L is said abdominal girth, A, B, C, D, E, G, H and I are predetermined constants, and e is a base of a natural logarithm.

Moreover, a twenty-third aspect of the invention is a visceral fat measuring method comprising: a subcutaneous fat measurement step of measuring a subcutaneous fat thickness by pressing a predetermined face against a living body surface at a pressure of not less than a predetermined pressure value; and a visceral fat calculation step of having an abdominal girth inputting step of inputting an abdominal girth, and calculating an amount of visceral fat by use of an expression 6 based on the subcutaneous fat thickness measured by said subcutaneous fat measuring step:

$$S = G \times L - H \times T_\infty + I \qquad \text{(Expression 6)}$$

where S is said amount of visceral fat, $T_\infty$ is the subcutaneous fat thickness measured by said subcutaneous fat measuring step, L is said abdominal girth, and G, H and I are predetermined constants.

A twenty-fourth aspect of the invention is a program of causing a computer to function as the following units of the visceral fat measuring apparatus according to the first aspect of the invention: the calculating unit of calculating the subcutaneous fat thickness in the condition where no pressure is applied to the living body surface, based on the subcutaneous fat thickness measured by said subcutaneous fat measuring unit; and the visceral fat calculating unit of calculating the information amount correlated with the visceral fat amount from the calculated subcutaneous fat thickness.

Moreover, a twenty-fifth aspect of the invention is a program of causing a computer to function as a visceral fat calculating unit, of the visceral fat measuring apparatus according to the fifth aspect of the invention, of calculating the amount of visceral fat by use of the expression 2 based on the subcutaneous fat thickness measured by said subcutaneous fat measuring unit and the pressure applied to said living body surface which pressure is measured by said pressing pressure measuring unit:

$$S=D\times((T-Be^{-CF})/(A-1)e^{-CF}+1))+E \qquad \text{(Expression 2)}$$

where S is said amount of visceral fat,

F is the pressure applied to said living body surface which pressure is measured by said pressing pressure measuring unit, T is the subcutaneous fat thickness measured by said subcutaneous fat measuring unit, A, B, C, D and E are the predetermined constants, and e is the base of the natural logarithm.

Moreover, a twenty-sixth aspect of the invention is a program of causing a computer to function as a visceral fat calculating unit, of the visceral fat measuring apparatus according to the sixth aspect of the invention, of calculating the amount of visceral fat by use of the expression 3 based on the subcutaneous fat thickness measured by said subcutaneous fat measuring unit:

$$S=D\times T_\infty+E \qquad \text{(Expression 3)}$$

where S is said amount of visceral fat, $T_\infty$ is the subcutaneous fat thickness measured by said subcutaneous fat measuring unit, and D and E are the predetermined constants.

Moreover, a twenty-seventh aspect of the invention is a program of causing a computer to function as a visceral fat calculating unit, of the visceral fat measuring apparatus according to the eighth aspect of the invention, of having an abdominal girth inputting unit of inputting an abdominal girth, and calculating the amount of visceral fat by use of the expression 5 based on the subcutaneous fat thickness measured by said subcutaneous fat measuring unit and the pressure applied to said living body surface which pressure is measured by said pressing pressure measuring unit:

$$S=G\times L-H\times (T-Be^{-CF})/((A-1)e^{-CF}+1))+I \qquad \text{(Expression 5)}$$

where S is said amount of visceral fat,

F is the pressure applied to said living body surface which pressure is measured by said pressing pressure measuring unit, T is the subcutaneous fat thickness measured by said subcutaneous fat measuring unit, L is said abdominal girth, A, B, C, D, E, G, H and I are the predetermined constants, and e is the base of the natural logarithm.

Moreover, a twenty-eighth aspect of the invention is a program of causing a computer to function as a visceral fat calculating unit, of the visceral fat measuring apparatus according to the ninth aspect of the invention, of having an abdominal girth inputting unit of inputting an abdominal girth, and calculating the amount of visceral fat by use of the expression 6 based on the subcutaneous fat thickness measured by said subcutaneous fat measuring unit:

$$S=G\times L-H\times T_\infty+I \qquad \text{(Expression 6)}$$

where S is said amount of visceral fat, $T_\infty$ is the subcutaneous fat thickness measured by said subcutaneous fat measuring unit, L is said abdominal girth, and G, H and I are the predetermined constants.

Moreover, a twenty-ninth aspect of the invention is a recording medium holding said program according to any one of the twenty-fourth to the twenty-eighth aspects of the invention, said recording medium being computer-processable.

The principle of the present invention will be briefly described.

The visceral fat measuring apparatus according to the present invention has a subcutaneous fat measuring unit that calculates the subcutaneous fat thickness by measuring the diffused and reflected light when light of wavelengths from the visible to a near infrared region is applied into a living body from the living body surface or calculates the subcutaneous fat thickness by measuring the reflected waves of ultrasonic waves. Moreover, the visceral fat measuring apparatus according to the present invention has a pressing pressure measuring unit that measures the pressure at which the subcutaneous fat measuring unit is pressed against the living body surface. In the description of the present invention, the pressure at which the subcutaneous fat measuring unit is pressed against the living body surface is called pressing pressure.

The relationship between the subcutaneous fat thickness measured by the subcutaneous fat measuring unit and the pressing pressure measured by the pressing pressure measuring unit is a curve as shown in FIG. 1. The curve differs among a plurality of different subcutaneous fat thicknesses in the condition where no pressing pressure is applied as shown in FIG. 1, and the curve is uniquely determined by pressing pressure and the subcutaneous fat thickness measured at the time. Therefore, by previously obtaining data of these curves and using the curve relationship, a subcutaneous fat thickness in the condition where no pressing pressure is applied can be obtained. For example, when a measured subcutaneous fat thickness is H1 and pressing pressure when the subcutaneous fat thickness is measured is P1, a subcutaneous fat thickness H2 in the condition where no pressing pressure is applied can be uniquely obtained from FIG. 1, with respect to H1. The calculating unit of the visceral fat measuring apparatus according to the present invention highly accurately calculates the subcutaneous fat thickness in the condition where no pressing pressure is applied, by use of a database holding information on the plurality of curves. From the thus calculated subcutaneous fat thickness in the condition where no pressing pressure is applied, the visceral fat calculating unit calculates the information amount correlated with a visceral fat amount.

Moreover, the relationship between subcutaneous fat thickness measured by the subcutaneous fat measuring unit and pressing pressure is, when the pressing pressure is high, as shown in FIG. 2. That is, when the pressing pressure is not less than a predetermined value, the measured subcutaneous fat thickness is a predetermined stable value as shown by the thick lines. The predetermined value of a pressing pressure increases as a subcutaneous fat thickness increases. Therefore, by setting as a prescribed value a pressure value higher than the predetermined value of the pressing pressure when the subcutaneous fat thickness is extremely thick, when the pressing pressure is not less than the prescribed value, the subcutaneous fat measuring unit can calculate the value of the subcutaneous fat thickness of the stable thick line part irrespective of the thickness of the subcutaneous fat. The curve of FIG. 2 is uniquely determined by the subcutaneous fat thickness of the stable thick line part. By previously obtaining the data of the curves of FIG. 2 and using the curve relationship, the subcutaneous fat thickness in the condition where no pressing pressure is applied can be obtained from the value of the subcutaneous fat thickness of the stable thick line part. For example, in FIG. 2, when the subcutaneous fat thickness measured in the condition where the pressing pressure P2 of the prescribed value is applied is H3, by using the curve relationship, the subcutaneous fat thickness H4 in the condition where no pressing pressure is applied can be uniquely obtained with respect to H3. While when the above-mentioned relationship of FIG. 1 is used, all the data on the curve is necessary, when the relationship of FIG. 2 is used, only the value of the subcutaneous fat thickness in the condition where no pressing pressure is applied need to be correlated with each subcutaneous fat thickness measured at a pressing pressure of not less than the prescribed value. The calculating unit of the visceral fat measuring apparatus according to the present invention in the case of FIG. 2 highly accurately calculates the subcutaneous fat thickness in the condition where no pressing pressure is applied, by use of the subcutaneous fat thickness measured at the pressing pressure of not less than the prescribed value and the database holding data of the subcutaneous fat thickness in the condition where no pressing pressure is applied with respect thereto. From the thus calculated subcutaneous fat thickness in the condition where no pressing pressure is applied, the visceral fat calculating unit calculates an information amount correlated with a visceral fat amount.

As described above, the visceral fat measuring apparatus according to the present invention uses the value of a subcutaneous fat thickness in the condition where no pressing pressure is applied which value is obtained as described above and excellent in repeatability.

Figure 1:
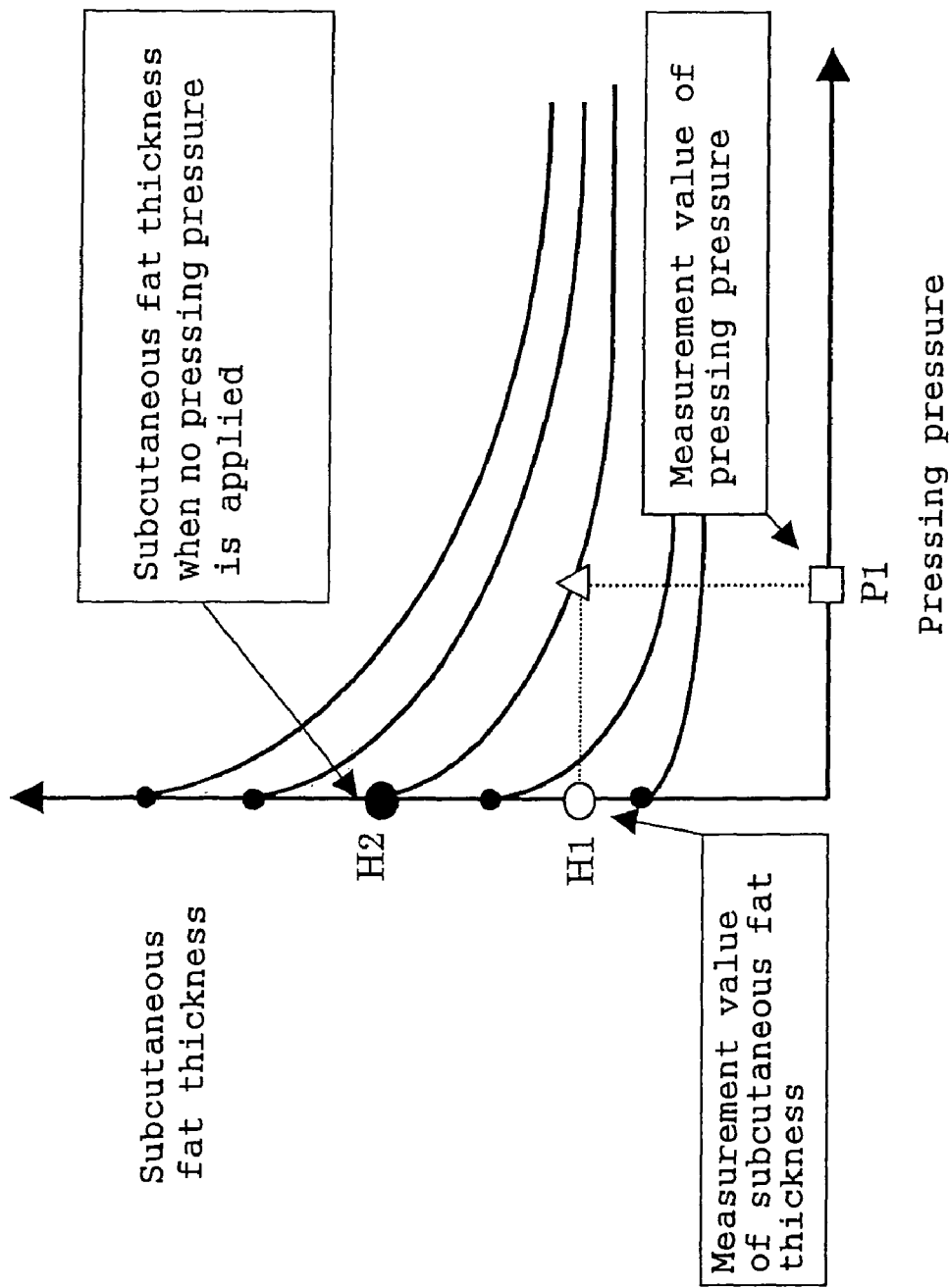
FIG. 1 is an explanatory view of the first principle of the present invention in which subcutaneous fat thickness in the condition where no pressing pressure is applied is derived from the relationship between pressing pressure and subcutaneous fat thickness.

EXPLANATION OF REFERENCE NUMERALS 1 living body surface
2 subcutaneous fat measuring unit
3 LED
4 first photodiode
5 second photodiode
6 pressing pressure measuring unit
7 calculating unit
8 ultrasonic element
9 soft body
10 domical lid
11 first wave
12 second wave
13 pressing pressure detecting unit
14 subcutaneous fat
15 visceral fat area
16 living body
17 abdominal girth measuring unit
18 string
19 reel
20 counter
21 protrusion
22 fixer
23 tension adjuster
24 visceral fat calculating unit
25 pressure/fat thickness-related data
26 stable fat thickness-related data
30 skin
31 muscle
51 visceral fat calculating unit
52 visceral fat calculating unit
53 visceral fat calculating unit
54 visceral fat calculating unit
55 visceral fat calculating unit

BEST MODE FOR CARRYING OUT THE INVENTION

Hereinafter, embodiments of the present invention will be described with reference to the drawings.

First Embodiment

Figure 3:
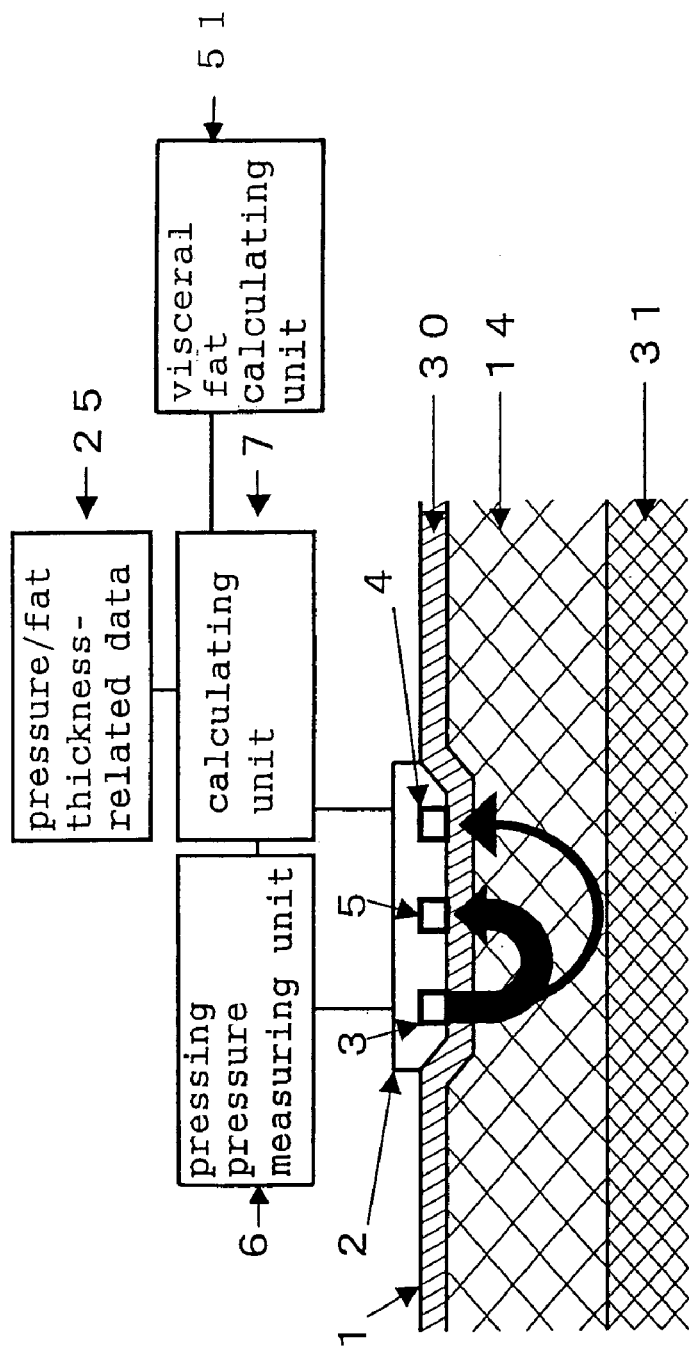
FIG. 3 is a structural view of a visceral fat measuring apparatus according to a first embodiment of the present invention.

FIG. 3 shows the structure of a visceral fat measuring apparatus according to a first embodiment of the present invention.

Figure 4:
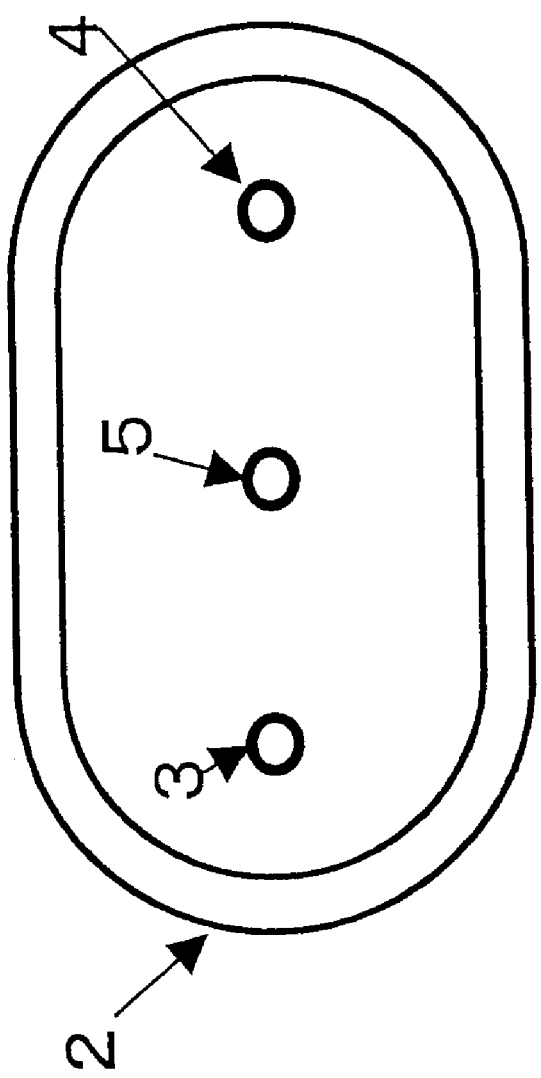
FIG. 4 is a plan view of a subcutaneous fat measuring unit according to the first embodiment of the present invention.

A subcutaneous fat measuring unit 2 placed on a living body surface 1 is an optical subcutaneous fat measuring apparatus. Inside this unit, an LED 3 with a center wavelength of 660 nm is disposed, and a first photodiode 4 and a second photodiode 5 are disposed at a distance of 45 mm and a distance of 22.5 mm from the LED 3, respectively. FIG. 4 shows a plan view of the subcutaneous fat measuring unit 2. The shape of the part of the subcutaneous fat measuring unit 2 that is in contact with the living body surface 1 is an oval whose both ends are semicircular as shown in FIG. 4. The oval surface that is in contact with the living body surface 1 is the face of the subcutaneous fat measuring unit 2 that is pressed against the living body surface 1 according to the present invention, and is made of or coated with a material whose reflectance in the region of the light emitting wavelength of the LED 3 is not more than 0.2. A pressing pressure measuring unit 6 that measures the pressing pressure applied to the living body surface 1 by the subcutaneous fat measuring unit 2 comprises a load cell and its peripheral circuits. A calculating unit 7 is provided that calculates a subcutaneous fat thickness in the condition where no pressing pressure is applied. Pressure/fat thickness-related data 25 is a database having, with respect to a plurality of subcutaneous thicknesses, information on the relationship, as shown in FIG. 1, between pressing pressure applied to the living body surface 1 in measuring subcutaneous fat thickness and the subcutaneous thickness measured at that time. Moreover, a visceral fat calculating unit 51 is provided that calculates the amount of visceral fat from subcutaneous fat thickness in the condition where no pressing pressure is applied. Reference numeral 14 represents subcutaneous fat. Reference numeral 30 represents skin. Reference numeral 31 represents muscle.

Next, the operation of the visceral fat measuring apparatus according to the first embodiment will be described, and also, an embodiment of a subcutaneous fat measuring method will be described.

From a light reception amount V1 of the first photodiode 4 and a light reception amount V2 of the second photodiode 5 obtained when light emitted from the LED 3, repetitively diffused and attenuated inside the living body and appearing again on the living body surface is measured, a subcutaneous fat thickness T is expressed as the following expression 7:

$$T = A \times (V1/V2) + B \qquad \text{(Expression 7)}$$

Here, A and B are uniquely determined from the wavelength and light emission characteristics of the LED 3 and light reception characteristics of the photodiodes 4 and 5. Here, it is necessary for the wavelength of the LED 3 only to be in a range of 600 to 1000 nm.

Figure 5:
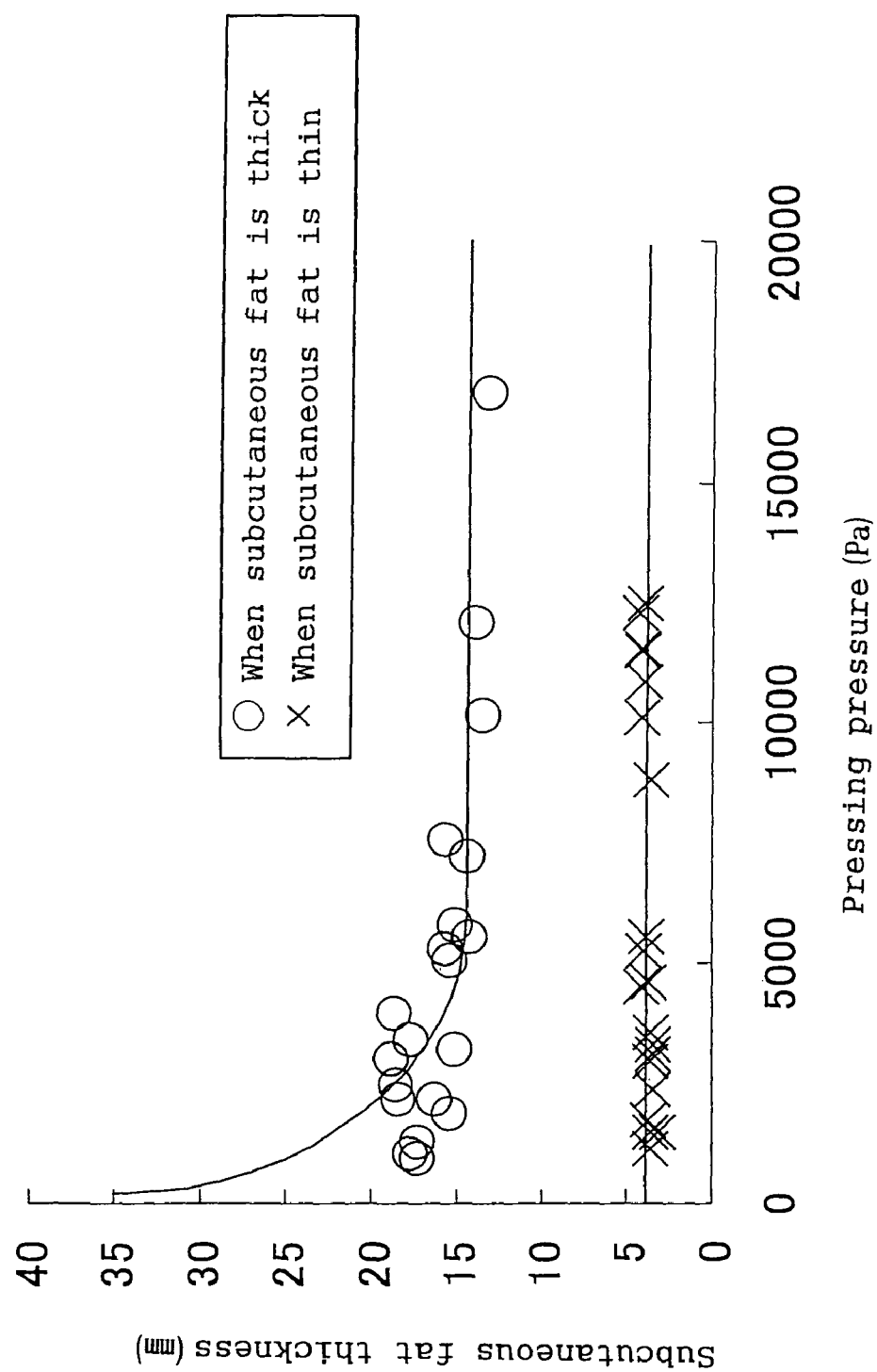
FIG. 5 is a view showing the relationship between pressing pressure and subcutaneous fat thickness in the first embodiment of the present invention.

The relationship between pressing pressure and subcutaneous fat thickness measured by use of the visceral fat measuring apparatus according to the first embodiment with respect to cases where subcutaneous fat is thick and where it is thin is as shown in FIG. 5, and it is apparent that the curve relationship between pressing pressure and subcutaneous fat thickness is present as shown in FIG. 1.

The pressure/fat thickness-related data 25 is a database having, with respect to a plurality of subcutaneous fat thicknesses, information on the relationship between pressing pressure and subcutaneous fat thickness measured by the subcutaneous fat measuring unit 2.

First, the pressure/fat thickness-related data 25 is created. With respect to each of a plurality of subcutaneous fat thicknesses in the condition where no pressing pressure is applied, the measurement of the subcutaneous fat thickness at a plurality of pressing pressures including the condition where no pressing pressure is applied and the measurement of the pressing pressure at the time of the subcutaneous fat thickness measurement are performed, and these pieces of data are obtained. In obtaining these pieces of data, it is not always necessary to perform all the measurements by the visceral fat measuring apparatus according to the first embodiment, but measurements may be performed by a different visceral fat measuring apparatus or subcutaneous fat thickness measuring apparatus whose measurement value is correlated with that of the visceral fat measuring apparatus according to the first embodiment. The values of the subcutaneous fat thickness measured at the obtained plurality of pressing pressures and the values of the pressing pressures at the time of the subcutaneous fat thickness measurement are converted into measurement values of the visceral fat measuring apparatus according to the first embodiment, and by associating them with the values of the plurality of subcutaneous fat thicknesses in the condition where no pressing pressure is applied, the pressure/fat thickness-related data 25 is created.

The visceral fat measuring apparatus according to the first embodiment performs subcutaneous fat thickness measurement by use of the pressure/fat thickness-related data 25 created as described above. The operation and method of the subcutaneous fat thickness measurement will be described.

Subcutaneous fat thickness measured by the subcutaneous fat measuring unit 2 is transmitted to the calculating unit 7, pressing pressure applied to the living body surface 1 by the subcutaneous fat measuring unit 2 when the subcutaneous fat thickness is measured is measured by the pressing pressure measuring unit 6, and the value of the pressing pressure is transmitted to the calculating unit 7. The calculating unit 7 calculates the value of the subcutaneous fat thickness when the pressing pressure is zero, that is, the subcutaneous fat thickness in the condition where no pressing pressure is applied, based on the measured pressing pressure and the measured subcutaneous fat thickness by use of the pressure/fat thickness-related data 25 created as described above.

Then, the subcutaneous fat thickness in the condition where no pressing pressure is applied which thickness is calculated by the calculating unit 7 is transmitted to the visceral fat calculating unit 51. The visceral fat calculating unit 51 calculates an information amount correlated with the visceral fat amount such as the amount of visceral fat from the transmitted subcutaneous fat thickness.

That is, the visceral fat calculating unit 51 calculates an amount S of visceral fat by use of the following expression 1:

$$S = D_0 \times T_0 + E_0 \qquad \text{(Expression 1)}$$

Here, S is the amount of visceral fat, $T_0$ is the calculated subcutaneous fat thickness in the condition where no pressing pressure is applied to the living body surface, and $D_0$ and $E_0$ are predetermined constants.

That is, the expression 1 indicates a correlation that the larger the subcutaneous fat thickness $T_0$ in the condition where no pressing pressure is applied is, the larger the amount S of visceral fat is.

The predetermined constants $D_0$ and $E_0$ are previously obtained, for example, by the following method:

The amount of visceral fat is calculated with respect to each of a plurality of subcutaneous fat thicknesses in the condition where no pressing pressure is applied. To calculate the amount of visceral fat, for example, the area of the parts that appear to be white in an X-ray CT image of a living body is obtained, and this is assumed to be the amount of visceral fat. In obtaining these pieces of data, it is not always necessary to perform all the measurements by the visceral fat measuring apparatus according to the first embodiment, but measurements may be performed by a different visceral fat measuring apparatus whose measurement value is correlated with that of the visceral fat measuring apparatus according to the first embodiment. In this manner, a plurality of pairs of values of subcutaneous fat thickness in the condition where no pressing pressure is applied and the amount of visceral fat are obtained. With respect to the plurality of pairs of values obtained in this manner, a regression analysis is performed and the predetermined constants $D_0$ and $E_0$ used for the expression 1 are determined.

As described above, since the visceral fat measuring apparatus according to the first embodiment is capable of accurately measuring subcutaneous fat thickness in the condition where no pressing pressure is applied, information correlated with the visceral fat amount such as the amount of visceral fat can be accurately measured.

Second Embodiment

Figure 6:
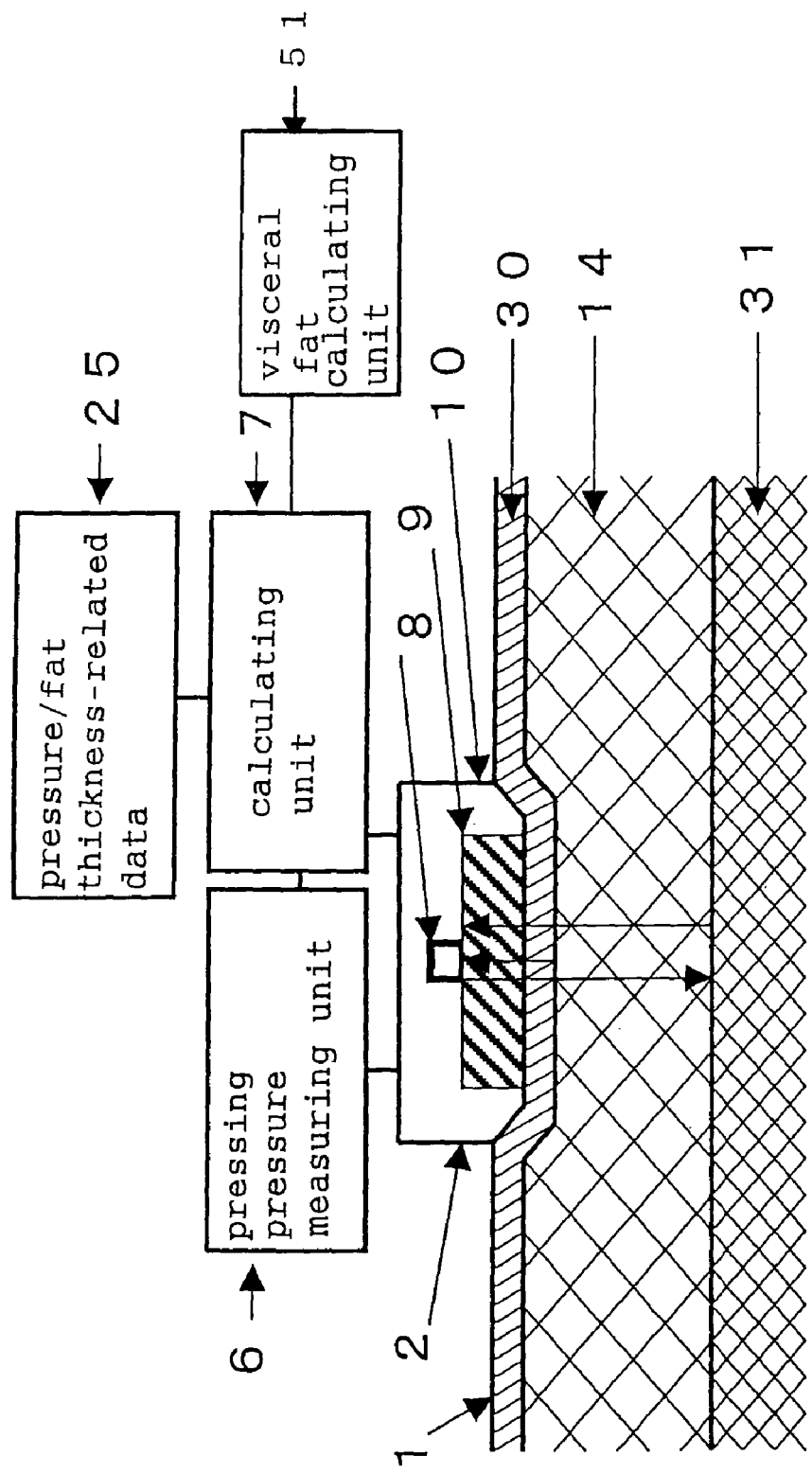
FIG. 6 is a structural view of a visceral fat measuring apparatus according to a second embodiment of the present invention.

FIG. 6 shows the structure of a visceral fat measuring apparatus according to a second embodiment of the present invention.

In the second embodiment, the subcutaneous fat measuring unit 2 according to the first embodiment is an ultrasonic measuring apparatus incorporating an ultrasonic element 8 and its peripheral circuits, and except this, the structure is similar to that of the first embodiment.

The enclosed space between the ultrasonic element 8 and the living body surface 1 is filled with a soft body 9, and the soft body is covered with a rugged domical lid 10. The soft body 9 is an ultrasonic delay line that delays ultrasonic waves, and is made of silicone rubber or resin or comprises gel or water covered with a soft transparent film. The shape of the surface where the domical lid 10 is in contact with the living body surface 1 is an oval whose both ends are semicircular like that of the subcutaneous fat measuring unit 2 according to the first embodiment shown in FIG. 4.

Next, the operation of the visceral fat measuring apparatus according to the second embodiment will be described.

Figure 7:
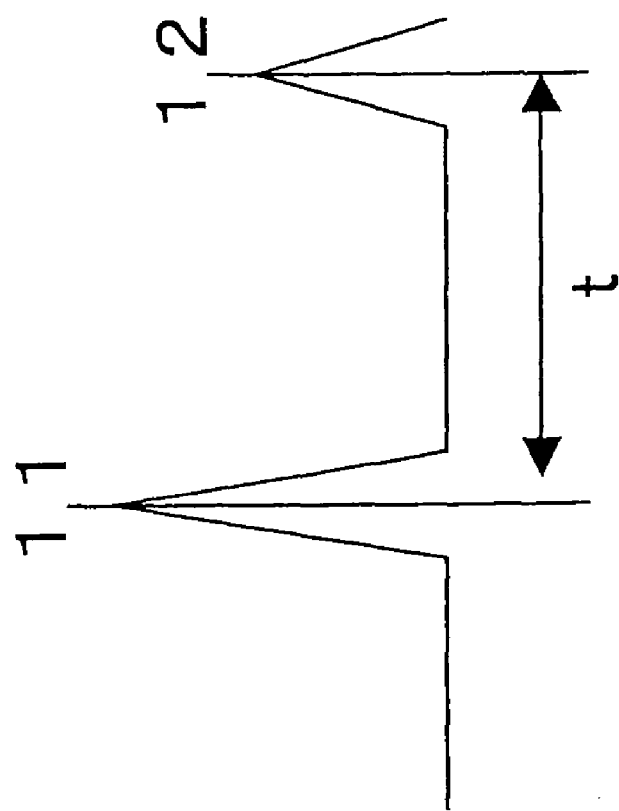
FIG. 7 is a conceptual view of waveforms observed by an ultrasonic element according to the second embodiment of the present invention.

The pulse waves emitted from the ultrasonic element 8 are reflected at the interface of each living body tissue, and the waveforms observed by the ultrasonic element 8 are as shown in FIG. 7. The waveforms line in the order of a first wave 11 which is a reflected wave from a skin 30 and a second wave 12 which is a reflected wave from the boundary between the subcutaneous fat 14 and the muscle 31. The subcutaneous fat thickness is half the product of the ultrasonic wave speed v and the time lag t between these two waves.

The soft body 9 not only improves the adhesion of the ultrasonic element 8 to the living body surface 1 but also is capable of reducing the influence of the multiple reflection inside the living body and the side lobes of the ultrasonic waves. Further, since surrounded by the ultrasonic element 8, the domical lid 10 and the living body surface 1, the soft body 9 does not change in shape even if the pressing pressure changes. Consequently, the position of the observed first wave 11 is stable irrespective of the pressing pressure, and only the position of the second wave 12 changes in response to changes in subcutaneous fat thickness. On the other hand, when the shape of the soft body 9 is not fixed, both the first wave 11 and the second wave 12 change in response to changes in subcutaneous fat thickness. Thus, a stable subcutaneous fat thickness can be measured compared to the case where the shape of the soft body 9 is not fixed.

Figure 8:
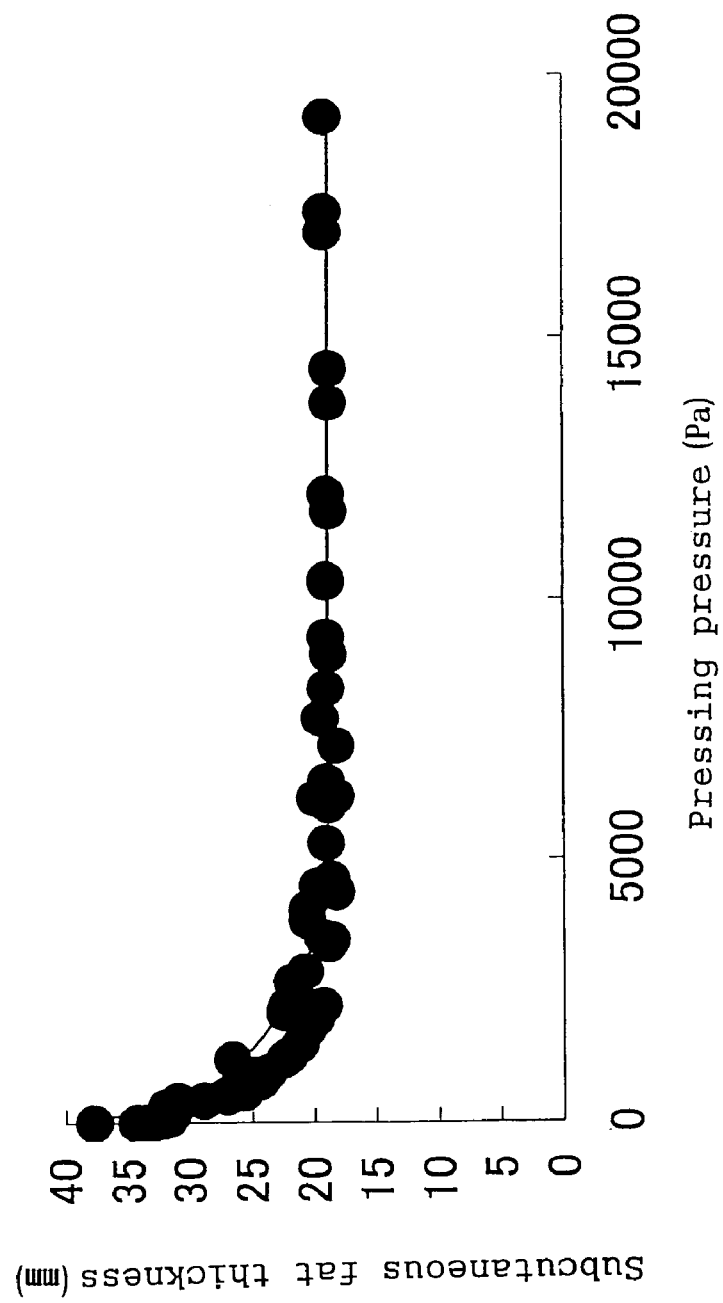
FIG. 8 is a view showing the relationship between pressing pressure measured by a pressing pressure measuring unit and subcutaneous fat thickness in the second embodiment of the present invention.

The relationship between subcutaneous fat thickness measured by the subcutaneous fat measuring unit 2 and pressing pressure measured by the pressing pressure measuring unit 6 in the second embodiment is shown in FIG. 8. Like in the first embodiment, it is apparent that the curve relationship between the pressing pressure and the subcutaneous fat thickness shown in FIG. 1 is present.

Like in the first embodiment, first, the database of the pressure/fat thickness-related data 25 is created. With respect to each of a plurality of subcutaneous fat thicknesses in the condition where no pressing pressure is applied, the measurement of the subcutaneous fat thickness at a plurality of pressing pressures including the condition where no pressing pressure is applied and the measurement of the pressing pressure at the time of the subcutaneous fat thickness measurement are performed, and these pieces of data are obtained. And by associating the values of the subcutaneous fat thicknesses measured at the obtained plurality of pressing pressures and the values of the pressing pressures at the time of the subcutaneous fat thickness measurement with the values of the plurality of subcutaneous fat thicknesses in the condition where no pressing pressure is applied, the pressure/fat thickness-related data 25 is created. Like in the first embodiment, it is not always necessary to use the organ fat measuring apparatus according to the present second embodiment in obtaining these pieces of data. When the measurement values obtained by a visceral fat measuring apparatus other than the visceral fat measuring apparatus according to the second embodiment are used, the pressure/fat thickness-related data 25 is created from values converted to the measurement values of the visceral fat measuring apparatus according to the second embodiment.

The visceral fat measuring apparatus according to the second embodiment performs subcutaneous fat thickness measurement by use of the pressure/fat thickness-related data 25 created as described above. Like in the first embodiment, the calculating unit 7 can calculate subcutaneous fat thickness in the condition where no pressing pressure is applied by use of the pressure/fat thickness-related data 25 based on subcutaneous fat thickness measured by the subcutaneous fat measuring unit 2 and pressing pressure measured by the pressing pressure measuring unit 6.

Then, the subcutaneous fat thickness in the condition where no pressing pressure is applied which thickness is calculated by the calculating unit 7 is transmitted to the visceral fat calculating unit 51. The visceral fat calculating unit 51 calculates the information amount correlated with the visceral fat amount such as the amount of visceral fat from the transmitted subcutaneous fat thickness. Since the visceral fat calculating unit 51 is similar to that of the first embodiment, a detailed description thereof is omitted.

While the subcutaneous fat measuring unit 2 according to the second embodiment measures subcutaneous fat thickness with one ultrasonic element 8, a plurality of ultrasonic elements 8 may be present, or it may be performed to scan the ultrasonic element 8 parallel to the living body surface 1 and measure the subcutaneous fat thickness from the obtained topographic image.

Third Embodiment

Figure 9:
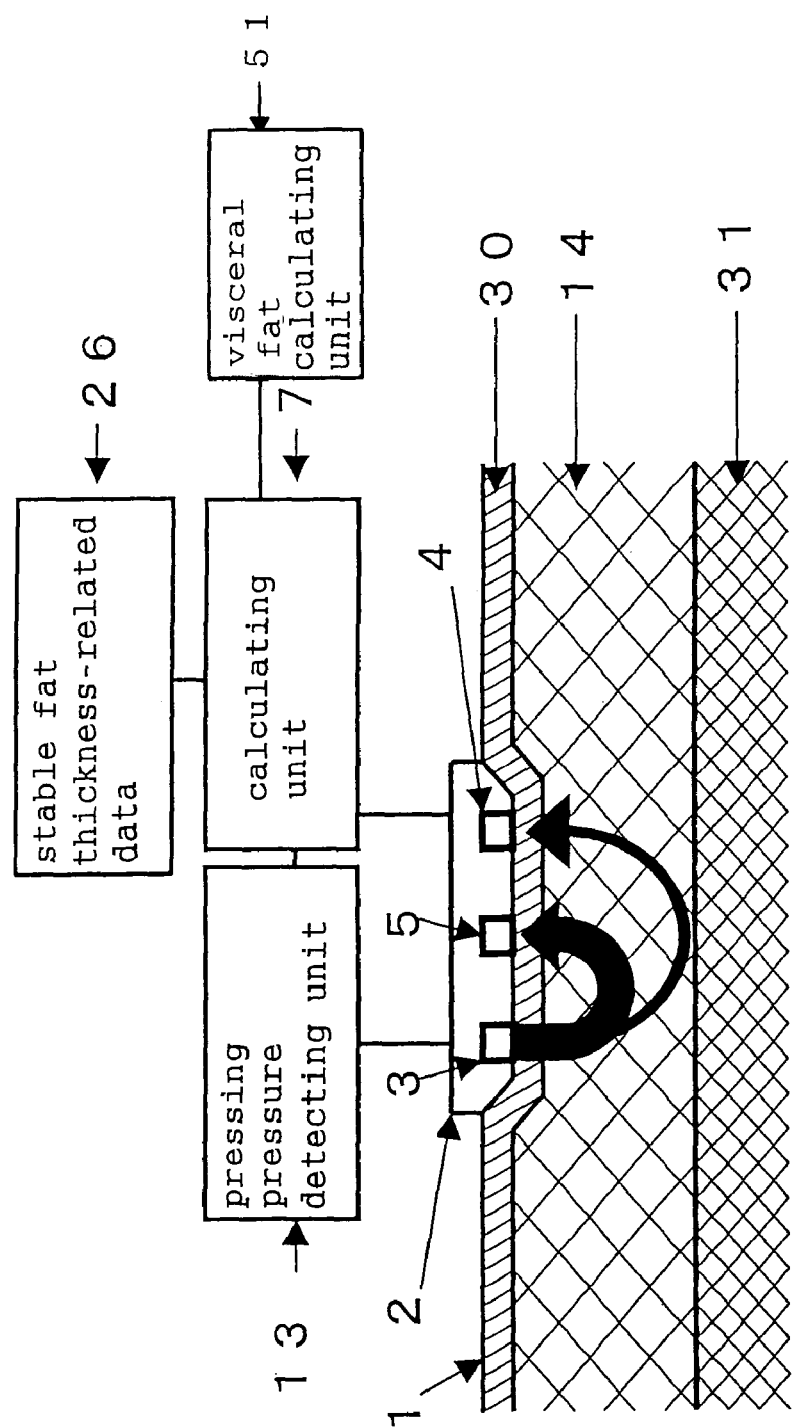
FIG. 9 is a structural view of a visceral fat measuring apparatus according to a third embodiment of the present invention.

FIG. 9 shows the structure of a visceral fat measuring apparatus according to a third embodiment of the present invention. Description on parts similar to those of the first embodiment are omitted, and only different points will be described.

Figure 2:
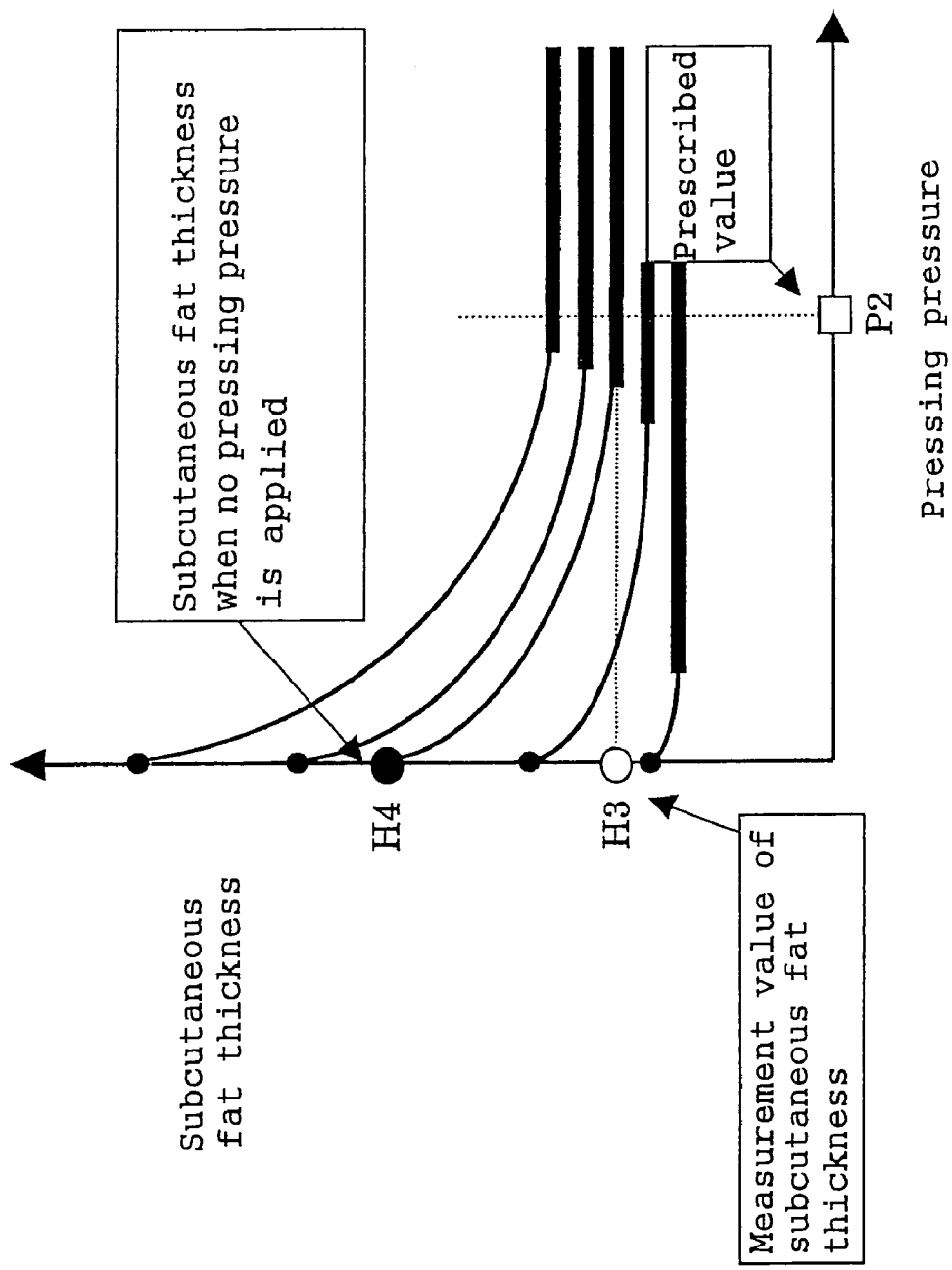
FIG. 2 is an explanatory view of the second principle of the present invention in which subcutaneous fat thickness in the condition where no pressing pressure is applied is derived from the relationship between pressing pressure and subcutaneous fat thickness.

The difference in structure from the first embodiment is the following two points: The pressing pressure measuring unit 6 is replaced with a pressing pressure detecting unit 13; and the pressure/fat thickness-related data 25 is replaced with stable fat thickness-related data 26. The pressing pressure detecting unit 13 comprises a spring and a switch, and the switch is turned on the pressing pressure applied to the living body surface 1 by the subcutaneous fat measuring unit 2 becomes not less than a prescribed value 10000 Pa. The prescribed value of pressing pressure is the predetermined pressure value of the present invention, and is the value of a pressing pressure at which a stable subcutaneous fat thickness measurement value is obtained irrespective of subcutaneous fat thickness. The stable fat thickness-related data 26 is a database having, with respect to a plurality of subcutaneous fat thicknesses, information on the relationship, as shown in FIG. 2, between subcutaneous fat thickness measured in the condition where a pressing pressure of not less than the prescribed value is applied and subcutaneous fat thickness in the condition where no pressing pressure is applied with respect to the subcutaneous fat thickness.

The operation of the visceral fat measuring apparatus according to the third embodiment will be described, and also, an embodiment of a subcutaneous fat measuring method will be described.

Figure 10:
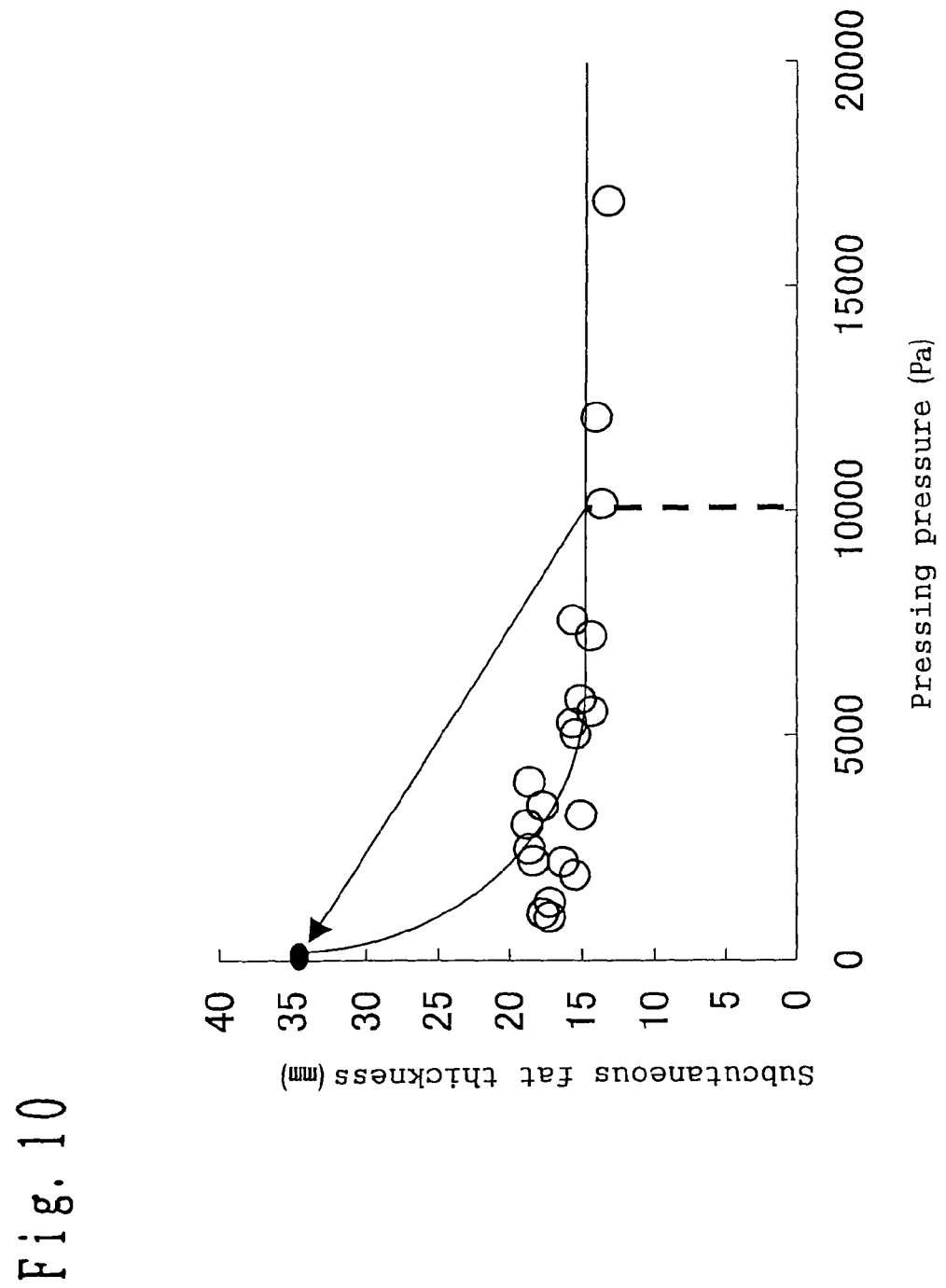
FIG. 10 is a view showing the relationship between pressing pressure and subcutaneous fat thickness in the third embodiment of the present invention.

First, the subcutaneous fat measuring unit 2 is pressed against the living body surface 1. FIG. 10 shows the relationship between measured pressing pressure and subcutaneous fat thickness. In this case, it is apparent that when the pressing pressure becomes not less than approximately 6000 Pa, the contraction of the subcutaneous fat thickness stops and the subcutaneous fat thickness is stabilized. By this, it is apparent that the curve relationship between the pressing pressure and the subcutaneous fat thickness shown in FIG. 2 is present.

The stable fat thickness-related data 26 is a database having, with respect to a plurality of subcutaneous fat thicknesses, information on the relationship between subcutaneous fat thickness measured by the subcutaneous fat measuring unit 2 when the pressing pressure is not less than 10000 Pa and subcutaneous fat thickness in the condition where no pressing pressure is applied with respect to the measured subcutaneous fat thickness.

First, the stable fat thickness-related data 26 is created. The measurement of a plurality of subcutaneous fat thicknesses when the pressing pressure is 10000 Pa and the measurement of the subcutaneous fat thickness in the condition where no pressing pressure is applied with respect to each of the plurality of subcutaneous fat thicknesses are performed, and these pieces of data are obtained. The measurement of the subcutaneous fat thickness in the condition where no pressing pressure is applied may be performed by a visceral fat measuring apparatus other than the visceral fat measuring apparatus according to the third embodiment. Then, by associating the plurality of subcutaneous fat thicknesses measured when the pressing pressure is 10000 Pa by the visceral fat measuring apparatus according to the third embodiment with the value of the subcutaneous fat thickness in the condition where no pressing pressure is applied with respect to each of the measured subcutaneous fat thicknesses, the stable fat thickness-related data 26 is created.

The visceral fat measuring apparatus according to the third embodiment performs subcutaneous fat thickness measurement by use of the stable fat thickness-related data 26 created as described above. The operation and method of the subcutaneous fat thickness measurement will be described.

When the pressing pressure becomes not less than 10000 Pa, the switch of the pressing pressure detecting unit 13 is turned on, and the data of the subcutaneous fat thickness measured by the subcutaneous fat measuring unit 2 is outputted from the subcutaneous fat measuring unit 2 to the calculating unit 7. The calculating unit 7 calculates the subcutaneous fat in the condition where no pressing pressure is applied from the data of the subcutaneous fat thickness measured by the subcutaneous fat measuring unit 2 by use of the stable fat thickness-related data 26 created as described above. In the case of FIG. 10, the subcutaneous fat thickness measured by the subcutaneous fat measuring unit 2 in the condition where the pressing pressure which is the prescribed value is 10000 Pa is 15 mm, and a value 35 mm is obtained by the calculation by the calculating unit 7 as the subcutaneous fat thickness in the condition where no pressing pressure is applied with respect to the subcutaneous fat thickness 15 mm.

Then, the subcutaneous fat thickness in the condition where no pressing pressure is applied which thickness is calculated by the calculating unit 7 is transmitted to the visceral fat calculating unit 51. The visceral fat calculating unit 51 calculates the information amount correlated with the visceral fat amount such as the amount of visceral fat from the transmitted subcutaneous fat thickness. Since the visceral fat calculating unit 51 is similar to the one described in the first embodiment, a detailed description thereof is omitted.

Next, the prescribed value of the pressing pressure will be described.

Figure 11:
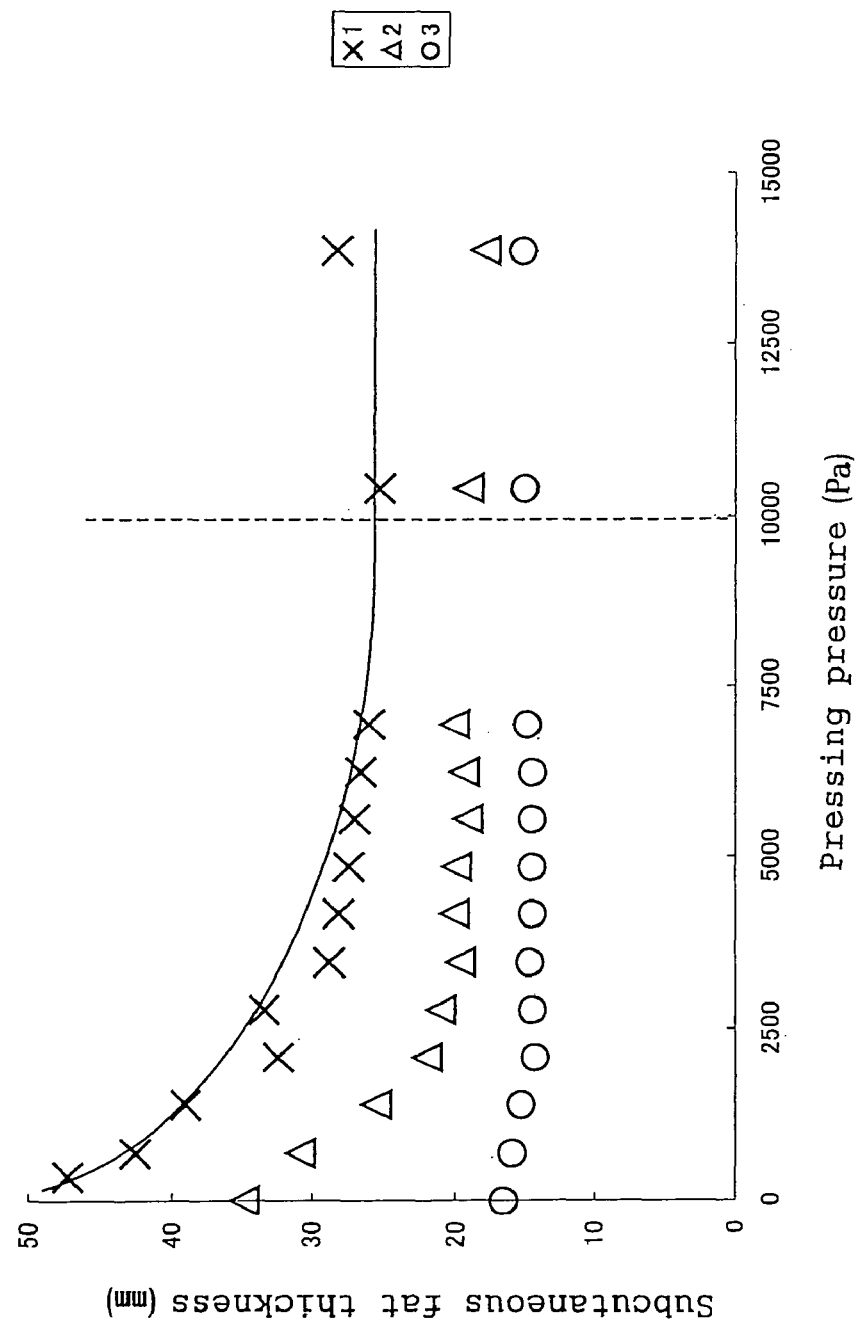
FIG. 11 is a view showing the relationship between pressing pressure and subcutaneous fat thickness for determining a prescribed value of pressing pressure in the third embodiment of the present invention.

FIG. 11 is a view showing the relationship between subcutaneous fat thickness and pressing pressure when the measurement is performed by a visceral fat measuring apparatus that is different only in the shape of the subcutaneous fat measuring unit 2 from that of the third embodiment, and shows three different subcutaneous fat thicknesses. Even when the shape of the subcutaneous fat measuring unit 2 is different, the relationship between the subcutaneous fat thickness and the pressing pressure is a curve relationship similar to that of the third embodiment.

In an abdomen where subcutaneous fat is thickest in a human body, the subcutaneous fat thickness is not more than 50 mm in substantially 100% of men and in approximately 95% of women. Therefore, from the curve which is the plot of the X marks in FIG. 1, it can be said that at a pressing pressure of not less than 10000 Pa, substantially all the persons' subcutaneous fat thicknesses are stabilized and the subcutaneous fat thickness measurement can be performed with excellent repeatability. For this reason, the prescribed value of the pressing pressure is 10000 Pa.

Like in the second embodiment, the subcutaneous fat measuring unit 2 may be one using an ultrasonic element.

Further, while the visceral fat measuring apparatus according to the third embodiment is provided with the pressing pressure detecting unit 13, it may be provided with no pressing pressure detecting unit 13. When the visceral fat measuring apparatus does not have the pressing pressure detecting unit 13, by pressing hard the subcutaneous fat measuring unit 2 against the living body surface 1 so that the pressing pressure exceeds the prescribed value and measuring the subcutaneous fat thickness by the subcutaneous fat measuring unit 2, a stabilized subcutaneous fat thickness can be measured even if the pressing pressure detecting unit 13 is not provided.

With the visceral fat measuring apparatus according to the third embodiment, measurement errors due to variations in pressing pressure during measurement are reduced and this enables stable measurement, so that measurement repeatability improves.

Moreover, an equal or better measurement can be performed with a simple structure of a spring and a switch without the use of an expensive load cell and peripheral circuits in the pressing pressure measuring unit.

Fourth Embodiment

Figure 12:
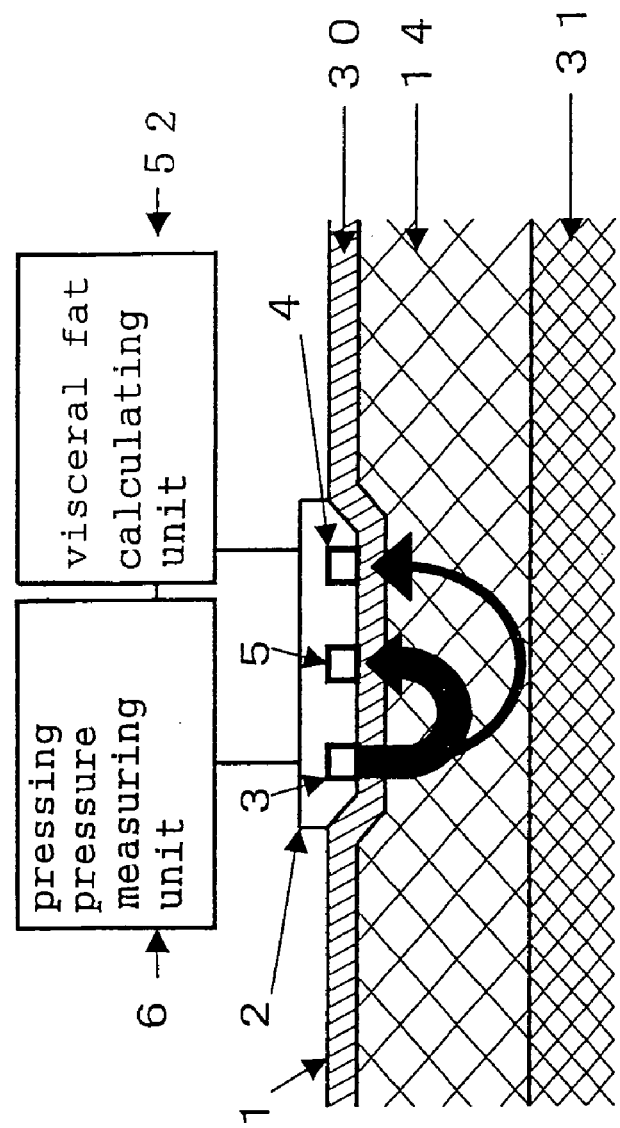
FIG. 12 is a structural view of a visceral fat measuring apparatus according to a fourth embodiment of the present invention.

FIG. 12 shows the structure of a visceral fat measuring apparatus according to a fourth embodiment of the present invention.

The visceral fat measuring apparatus according to the fourth embodiment is different from the visceral fat measuring apparatus of FIG. 3 according to the first embodiment in the following points: The visceral fat measuring apparatus according to the fourth embodiment is not provided with the pressure/fat thickness-related data 25 unlike the visceral fat measuring apparatus of FIG. 3. Moreover, it is provided with a visceral fat calculating unit 52 instead of the calculating unit 7. Except these, it is similar to the visceral fat measuring apparatus of FIG. 3 according to the first embodiment.

Next, the operation of the present embodiment will be described.

Subcutaneous fat thickness measured by the subcutaneous fat measuring unit 2 is transmitted to the visceral fat calculating unit 52, the pressing pressure applied to the living body surface 1 by the subcutaneous fat measuring unit 2 when the subcutaneous fat thickness is measured is measured by the pressing pressure measuring unit 6, and the value of the pressing pressure is transmitted to the visceral fat calculating unit 52. The visceral fat calculating unit 52 calculates the information amount correlated with the visceral fat amount such as the amount of visceral fat from the values of the subcutaneous fat thickness measured by the subcutaneous fat measuring unit 2 and the pressing pressure measured by the pressing pressure measuring unit 6. That is, the visceral fat calculating unit 52 calculates the amount S of visceral fat by use of the following expression 2:

$$S = D \times ((T - Be^{-CF})/(A-1)e^{-CF} + 1)) + E \qquad \text{(Expression 2)}$$

Here, S is the amount of visceral fat,

F is the pressure applied to the living body surface which pressure is measured by the pressing pressure measuring unit, T is the subcutaneous fat thickness measured by the subcutaneous fat measuring unit, A, B, C, D and E are predetermined constants, and e is the base of a natural logarithm.

The subcutaneous fat thickness T measured by the subcutaneous fat measuring unit varies according to the pressing pressure F. That is, as the pressing pressure F increases, the measured subcutaneous fat thickness T decreases, and as the pressing pressure F decreases, the measured subcutaneous fat thickness T increases. The expression 2 is to correct the variations in the subcutaneous fat thickness T due to variations in the pressing pressure F to obtain an accurate amount S of visceral fat.

The expression 2 will be described.

When the subcutaneous fat thickness measured by the subcutaneous fat measuring unit when the pressing pressure is not less than the prescribed value is $T_\infty$, the subcutaneous fat thickness in the condition where no pressing pressure is applied is $T_0$, the subcutaneous fat thickness measured by the subcutaneous fat measuring unit when the pressing pressure is an arbitrary value is T, and the pressing pressure is F, the following relationship holds thereamong:

$$T = (T_0 - T_\infty)e^{-CF} + T_\infty$$

Here, C is a predetermined constant C is set, for example, to a value that satisfies $e^{-10000C} = 10^{-3}$ in consideration of the case where the pressing pressure is 10000 Pa, but it is not limited thereto. It may be a value other than the value that satisfies $e^{-10000C} = 10^{-3}$ as long as it is a value such that $e^{-10000C}$ is a negligibly low value when the pressing pressure is 10000 Pa.

This expression indicates that the subcutaneous fat thickness T measured by the subcutaneous fat measuring unit exponentially decreases as the pressing pressure increases. It also indicates that when the pressing pressure becomes not less than the prescribed value, the subcutaneous fat thickness substantially coincides with $T_\infty$.

Using predetermined constants A and B, $T_\infty$ can be expressed as follows:

$$T_0 = AT_\infty + B$$

Here, A and B are constants depending on the configuration of the subcutaneous fat measuring unit. In a case where the subcutaneous fat measuring unit 2 according to the present embodiment is used, when the unit of the subcutaneous fat thickness is mm, A is 1.4 and B is 0.5. Substituting this expression into the expression of relationship among T, $T_0$ and $T_\infty$, $$\begin{aligned} T &= (T_0 - T_\infty)e^{-CF} + T_\infty \\ &= ((A-1)T_\infty + B)e^{-CF} + T_\infty \\ &= T_\infty((A-1)e^{-CF} + 1) + Be^{-CF} \end{aligned}$$

Therefore, obtaining $T_\infty$, $$T_\infty = (T - Be^{-CF})/((A-1)e^{-CF} + 1)$$

The expression 2 can be obtained by substituting this expression into an expression 3 described later.

As described above, the visceral fat measuring apparatus according to the fourth embodiment is capable of accurately measuring information correlated with a visceral fat amount such as the amount of visceral fat by properly correcting the variations in subcutaneous fat thickness due to variations in pressing pressure.

Fifth Embodiment

Figure 13:
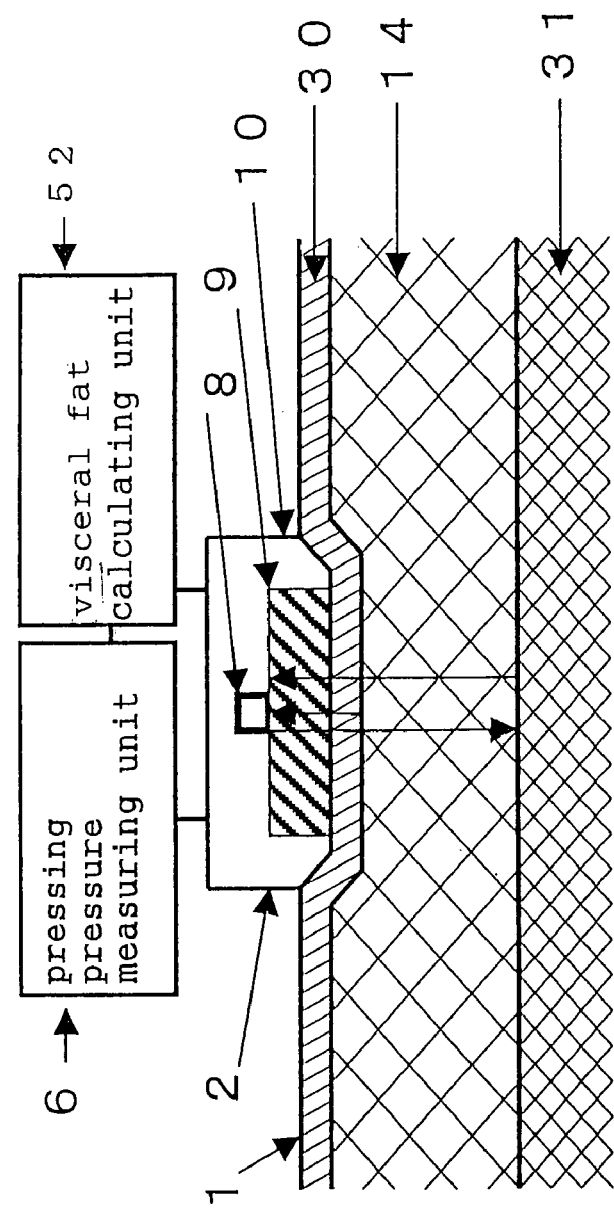
FIG. 13 is a structural view of a visceral fat measuring apparatus according to a fifth embodiment of the present invention.

FIG. 13 shows the structure of a visceral fat measuring apparatus according to a fifth embodiment of the present invention.

The visceral fat measuring apparatus according to the fifth embodiment is different from the visceral fat measuring apparatus of FIG. 6 according to the second embodiment in the following points: The visceral fat measuring apparatus according to the fifth embodiment is not provided with the pressure/fat thickness-related data 25 unlike the visceral fat measuring apparatus of FIG. 3. Moreover, it is provided with the visceral fat calculating unit 52 instead of the calculating unit 7. Except these, it is similar to the visceral fat measuring apparatus of FIG. 6 according to the second embodiment.

Next, the operation of the present embodiment will be described.

The subcutaneous fat measuring unit 2 measures subcutaneous fat thickness, and pressing pressure measuring unit 6 measures pressing pressure. The visceral fat calculating unit 52 calculates the information amount correlated with the visceral fat amount such as the amount of visceral fat from the values of the subcutaneous fat thickness measured by the subcutaneous fat measuring unit 2 and the pressing pressure measured by the pressing pressure measuring unit 6. The visceral fat calculating unit 52 is similar to that of the first embodiment.

As described above, the visceral fat measuring apparatus according to the fifth embodiment is capable of accurately measuring information correlated with a visceral fat amount such as the amount of visceral fat by properly correcting the variations in subcutaneous fat thickness due to variations in pressing pressure like that of the fourth embodiment.

Sixth Embodiment

Figure 14:
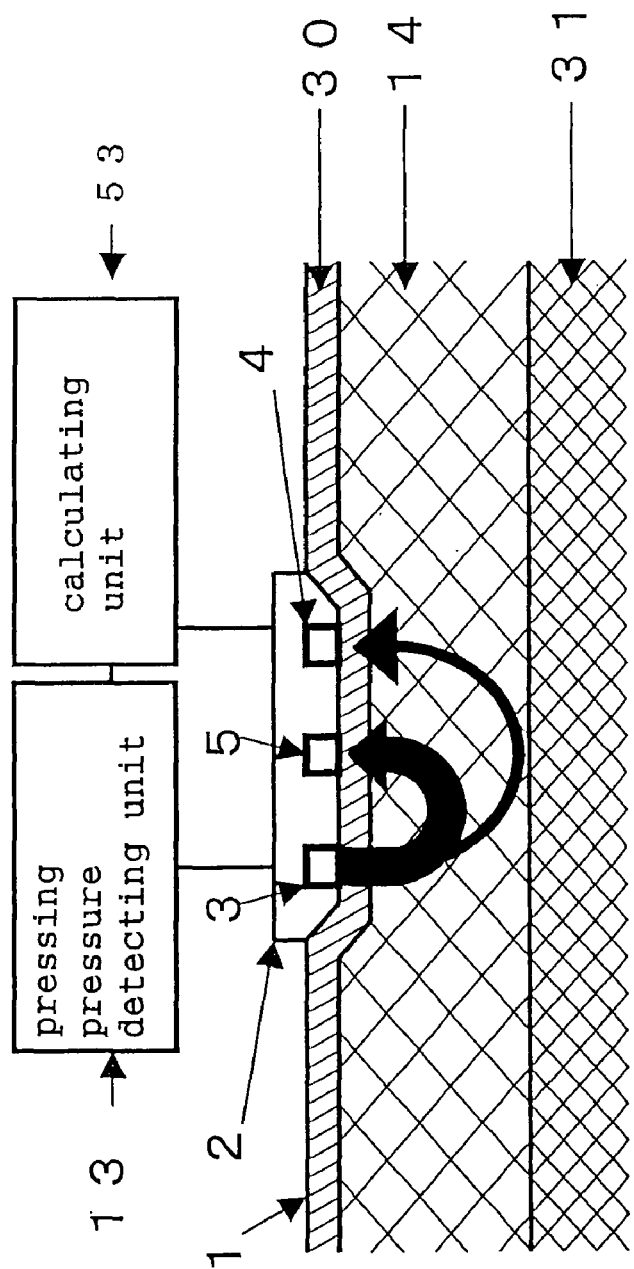
FIG. 14 is a structural view of a visceral fat measuring apparatus according to a sixth embodiment of the present invention.

FIG. 14 shows the structure of a visceral fat measuring apparatus according to a sixth embodiment of the present invention.

The visceral fat measuring apparatus according to the sixth embodiment is different from the visceral fat measuring apparatus of FIG. 9 according to the third embodiment in the following points: The visceral fat measuring apparatus according to the sixth embodiment is not provided with the stable fat thickness-related data 26 unlike the visceral fat measuring apparatus of FIG. 9. Moreover, it is provided with the visceral fat calculating unit 53 instead of the calculating unit 7. Except these, it is similar to the visceral fat measuring apparatus of FIG. 9 according to the third embodiment.

Next, the operation of the present embodiment will be described.

Subcutaneous fat thickness measured by the subcutaneous fat measuring unit 2 is transmitted to the visceral fat calculating unit 52. The subcutaneous fat thickness measured by the subcutaneous fat measuring unit 2 is a subcutaneous fat thickness measured when the pressing pressure is not less than the prescribed value as described in the third embodiment, and a stable measurement value is obtained irrespective of the thickness of the subcutaneous fat.

The visceral fat calculating unit 53 calculates the information amount correlated with a visceral fat amount such as the amount of visceral fat from the subcutaneous fat thickness measured by the subcutaneous fat measuring unit 2 when the pressing pressure is not less than the prescribed value. That is, the visceral fat calculating unit 53 calculates the amount S of visceral fat by use of the following expression 3:

$$S = D \times T_\infty + E \quad \text{(Expression 3)}$$

Here, S is the amount of visceral fat, $T_\infty$ is the subcutaneous fat thickness measured by the subcutaneous fat measuring unit, and D and E are predetermined constants.

That is, the expression 3 indicates a correlation that the larger the subcutaneous fat thickness $T_\infty$ measured when the pressing pressure is not less than the prescribed value is, the larger the amount S of visceral fat is.

The predetermined constants D and E are previously obtained by the following method:

The amount of visceral fat is calculated with respect to each of a plurality of subcutaneous fat thicknesses in the condition where no pressing pressure is applied. To calculate the amount of visceral fat, for example, the area of the parts that appear to be white in an X-ray CT image of a living body is obtained, and this is assumed to be the amount of visceral fat. In obtaining these pieces of data, it is not always necessary to perform all the measurements by the visceral fat measuring apparatus according to the sixth embodiment, but measurements may be performed by a different visceral fat measuring apparatus whose measurement value is correlated with that of the visceral fat measuring apparatus according to the sixth embodiment. In this manner, a plurality of pairs of values of the subcutaneous fat thickness in the condition where the pressing pressure is not less than the prescribed value and the amount of visceral fat are obtained. With respect to the plurality of pairs of values obtained in this manner, a regression analysis is performed and the predetermined constants D and E used for the expression 3 are determined.

As described above, since the visceral fat measuring apparatus according to the sixth embodiment is capable of accurately measuring subcutaneous fat when the pressing pressure is not less than the prescribed value, information correlated with the visceral fat amount such as the amount of visceral fat can be accurately measured.

Seventh Embodiment

Figure 15:
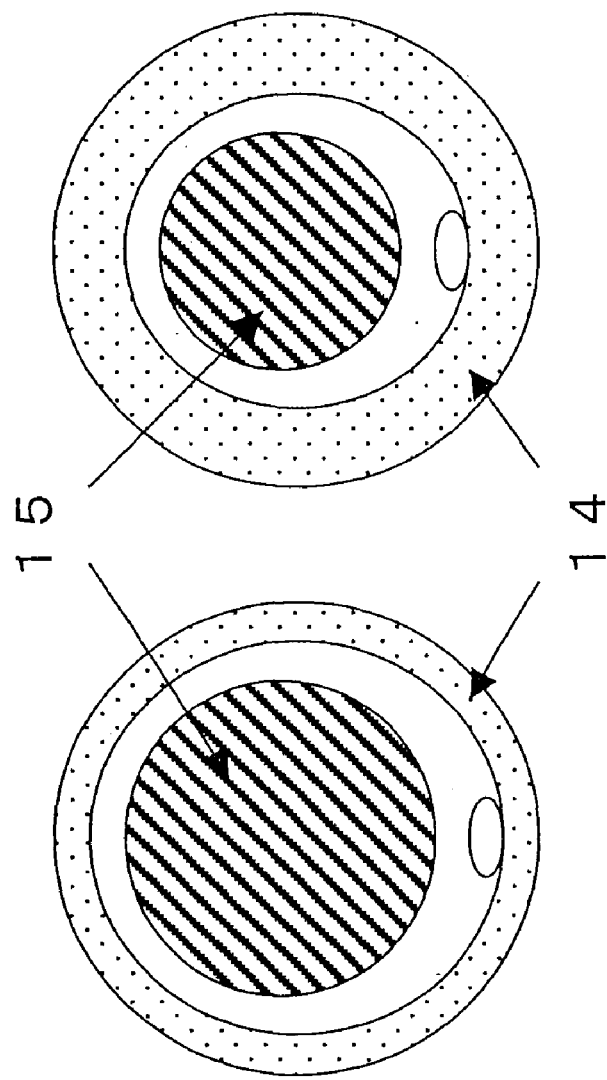
FIG. 15 shows cross-sectional views of torsos of living bodies showing the relationship between a visceral fat area and subutaneous fat thickness for determining an information amount correlated with a visceral fat amount in a seventh embodiment of the present invention.

A visceral fat measuring method according to a seventh embodiment of the present invention will be described with reference to FIG. 15. FIG. 15 shows cross-sectional views of abdominal parts when the torso of a living body is regarded as substantially circular. Even when the abdominal girth is the same, there is a significant difference in the visceral fat area 15 contained inside between in the case of the left view where the subcutaneous fat 14 is thin and in the case of the right view where the subcutaneous fat 14 is thick.

Here, it is necessary to correct variations in the subcutaneous fat 14 with respect to the abdominal girth. Since, to do this, a subcutaneous fat thickness in the condition where no force is applied to the living body surface is necessary, any of the visceral fat measuring apparatuses according to the first to third embodiments is used for the measurement of the subcutaneous fat thickness in the condition where no pressing pressure is applied.

Further, abdominal girth L is measured with a measure or the like, and since a cross section of a living body in the vicinity of the navel is substantially circular, from the abdominal girth L and subcutaneous fat thickness $T_0$ in the condition where no pressing pressure is applied, abdominal girth L' excluding the subcutaneous fat thickness is obtained as shown by the expression 8:

$$L' = L - 2 \times \pi \times T_0 \quad \text{(Expression 8)}$$

By this method, the abdominal girth L' excluding the subcutaneous fat thickness can be obtained which abdominal girth L' is an information amount correlated with the visceral fat amount and serving as an index of an accurate visceral fat amount where variations due to the difference in subcutaneous fat thickness are suppressed.

When the amount of visceral fat is S, it can be expressed as follows by use of the abdominal girth L' excluding the subcutaneous fat thickness:

$$S = AL' + B$$

Here, A and B are predetermined constants.

Substituting this expression into the expression 8, the amount S of visceral fat can be expressed as follows:

$$S = A(L - 2 \times \pi \times T_0) + B$$
$$= AL - 2 \times \pi \times A \times T_0 + B$$

Substituting G0 for A, H0 for $2 \times \pi \times A$, and $I_0$ for B, the expression 4 to obtain the amount S of visceral fat is obtained.

$$S = G_0 \times L - H_0 \times T_0 + I_0 \quad \text{(Expression 4)}$$

Here, S is the amount of visceral fat,
$T_0$ is the calculated subcutaneous fat thickness in the condition where no pressure is applied to the living body surface,
L is the abdominal girth, and
$G_0$, $H_0$ and $I_0$ are predetermined constants.

Thus, the amount S of visceral fat can be obtained by use of the expression 4. Moreover, in the expression 4, the predetermined constants $G_0$, $H_0$ and $I_0$ can be determined by previously obtaining a plurality of groups of values of S, L and $T_0$ and performing a regression analysis.

Moreover, since the subcutaneous fat thickness is not uniform around the entire abdomen as shown in FIG. 15, to obtain the abdominal girth L' excluding the subcutaneous fat thickness, the subcutaneous fat thickness $T_\infty$ when the pressing pressure is not less than the prescribed value may be used. When the abdominal girth excluding the subcutaneous fat thickness by use of the subcutaneous fat thickness $T_\infty$ when the pressing pressure is not less than the prescribed value is L", L" can be expressed by the following expression:

$$L' = L - 2 \times \pi \times T_\infty$$

Substituting this expression into S=AL'+B expressing the amount of visceral fat, the amount of visceral fat can be expressed as follows:

$$S = A(L - 2 \times \pi \times T_\infty) + B$$
$$= AL - 2 \times \pi \times A \times T_\infty + B$$

Here, substituting G for A, H for $2 \times \pi \times A$ and I for B, the expression 6 to obtain the amount S of visceral fat is obtained.

$$S = G \times L - H \times T_\infty + I \quad \text{(Expression 6)}$$

Here, S is the amount of visceral fat,
$T_\infty$ is the subcutaneous fat thickness measured by the subcutaneous fat measuring unit when the pressing pressure is not less than the prescribed value,
L is the abdominal girth, and
G, H and I are predetermined constants.

By using the expression 6, the amount of visceral fat can be accurately obtained from the subcutaneous fat thickness $T_\infty$ measured by the subcutaneous fat measuring unit when the pressing pressure is not less than the prescribed value. Moreover, in the expression 6, the predetermined constants G, H and I can be determined by previously obtaining a plurality of groups of values of S, L and $T_\infty$ and performing a regression analysis.

When the subcutaneous fat thickness measured by the subcutaneous fat measuring unit when the pressing pressure is not less than the prescribed value is $T_\infty$, the subcutaneous fat thickness in the condition where no pressing pressure is applied is $T_0$, the subcutaneous fat thickness measured by the subcutaneous fat measuring unit when the pressing pressure is an arbitrary value is T, and the pressing pressure is F, the following relationship holds thereamong:

$$T = (T_0 - T_\infty)e^{-CF} + T_\infty$$

Here, C is a predetermined constant. C is set, for example, to a value that satisfies $e^{-10000C} = 10^{-3}$ in consideration of the case where the pressing pressure is 10000 Pa, but it is not limited thereto. It may be a value other than the value that satisfies $e^{-10000C} = 10^{-3}$ as long as it is a value such that $e^{-10000C}$ is a negligibly low value when the pressing pressure is 10000 Pa.

This expression indicates that the subcutaneous fat thickness T measured by the subcutaneous fat measuring unit exponentially decreases as the pressing pressure increases. It also indicates that when the pressing pressure becomes not less than the prescribed value, the subcutaneous fat thickness substantially coincides with $T_\infty$.

Using predetermined constants A and B, $T_0$ can be expressed as follows:

$$T_0 = AT_\infty + B$$

Here, A and B are constants depending on the configuration of the subcutaneous fat measuring unit. In a case where the subcutaneous fat measuring unit 2 according to the present embodiment is used, when the unit of the subcutaneous fat thickness is mm, A is 1.4 and B is 0.5. Substituting this expression into the relational expression among T, $T_0$ and $T_\infty$, $$T = (T_0 - T_\infty)e^{-CF} + T_\infty$$
$$= ((A - 1)T_\infty + B)e^{-CF} + T_\infty$$
$$= T_\infty((A - 1)e^{-CF} + 1) + Be^{-CF}$$

Therefore, obtaining $T_\infty$, $$T_\infty = (T - Be^{-CF})/((A-1)e^{-CF} + 1)$$

By substituting this expression into the expression 6, an expression 5 is obtained.

$$S = G \times L - H \times (T - Be^{-CF})/((A-1)e^{-CF} + 1) + I \quad \text{(Expression 5)}$$

Here, S is the amount of visceral fat,
F is the pressure applied to the living body surface which pressure is measured by the pressing pressure measuring unit,
T is the subcutaneous fat thickness measured by the subcutaneous fat measuring unit,
L is the abdominal girth,
A, B, C, D, E, G, H and I are predetermined constants, and
e is the base of a natural logarithm.

By using the expression 5, variations in the subcutaneous fat thickness T measured by the subcutaneous fat measuring unit due to the pressing pressure F can be corrected even when the pressing pressure is not more than the prescribed value, so that the visceral fat amount can be accurately calculated.

While the conventional report (Yuji MATSUZAWA and 13 others, "Atarashii himan no hantei to himansho no shindan kijun (new obesity determination and obesity diagnosis criteria), *Himan Kenkyu* (obesity research), Vol. 6, No. 1, 2000 <Committee Report> Obesity Diagnosis Criteria Examination Committee of the Japan Society for the Study of Obesity) uses the waist girth as the information amount correlated with the visceral fat area, the present invention uses the abdominal girth which is the distance around the abdomen at the navel and is higher in measurement repeatability than the waist girth.

Eighth Embodiment

Figure 16:
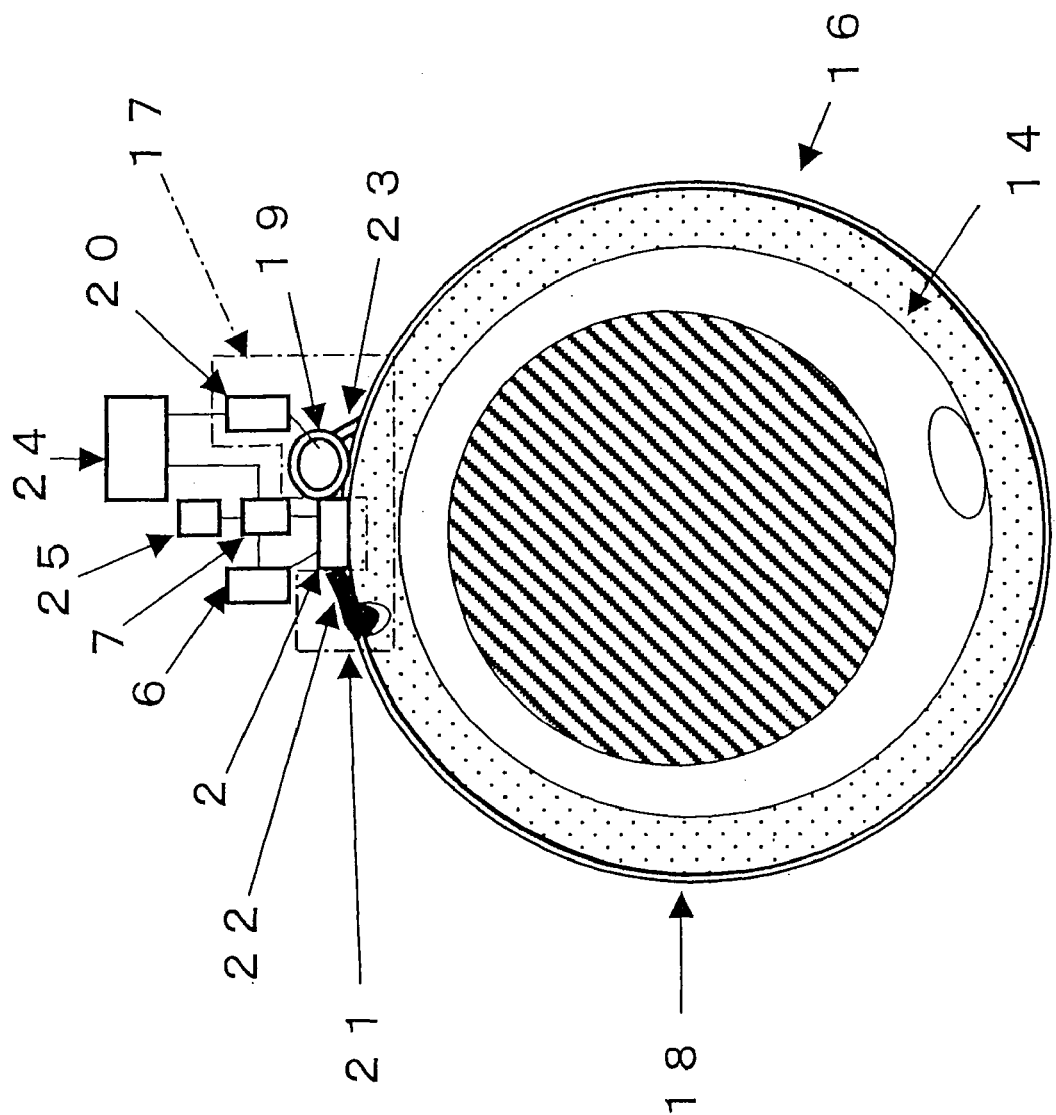
FIG. 16 is a structural view of a visceral fat measuring bodies according to an eighth embodiment of the present invention.

FIG. 16 shows the structure of a visceral fat measuring apparatus according to an eighth embodiment of the present invention. Descriptions of parts similar to those of the first to third embodiments are omitted, and only different parts will be described.

The structure is different from that of the first to third embodiments in that an abdominal girth measuring unit 17 that measures the abdominal girth of a living body 16 is provided and that a visceral fat calculating unit 24 is provided. The abdominal girth measuring unit 17 is provided with a string 18, a reel 19 that winds up the string 18, a counter 20 that counts the number of rotations of the reel 19, and a fixer 22. The fixer 22 has a protrusion 21 that is pressed against the navel hole, and the protrusion 21 defines the position of the visceral fat measuring apparatus on the living body surface. The abdominal girth measuring unit 17 has a part that winds the string 18 one turn around the living body 16 and fixes it again. The reel 19 has a tension adjuster 23 that pulls the string 18 at a predetermined tension, thereby reducing errors of the abdominal girth measurement due to the string 18 being sagged when wound one turn around the living body 16 or to the spring 18 being dug into the living body 16 because of being pulled too hard.

The operation of the visceral fat measuring apparatus according to the eighth embodiment will be described.

The abdominal girth L is measured by the counter 20 counting the number of times the reel 19 rotates from the condition where the string 18 is wound up around the reel 19 to when it is wound one turn around the living body 16 and fixed by the abdominal girth measuring unit 17. The abdominal girth L may be measured by counting the marks provided on the string 18 at predetermined intervals instead of by counting the number of rotations of the reel 19.

Since the cross section of a living body in the vicinity of the navel is substantially circular, from the measured abdominal girth L and the subcutaneous fat thickness T in the condition where no pressing pressure is applied, the abdominal girth L' excluding the subcutaneous fat thickness can be obtained by use of the expression 8 described in the seventh embodiment. By this method, the visceral fat calculating unit 24 calculates the abdominal girth L' excluding the subcutaneous fat thickness. Thereby, the abdominal girth L' excluding the subcutaneous fat thickness can be obtained which abdominal girth L' is an information amount serving as an index of an accurate visceral fat where variations in subcutaneous fat thickness among individuals are corrected.

The visceral fat calculating unit 24 obtains the amount of visceral fat by use of the expression 4 described in the seventh embodiment from the measured abdominal girth L and the subcutaneous fat thickness T in the condition where no pressing pressure is applied.

As described above, the visceral fat measuring apparatus according to the eighth embodiment is capable of accurately obtaining the abdominal girth L' excluding the subcutaneous fat thickness and the amount of visceral fat.

While the pressing pressure measuring unit 6 and the pressure/fat thickness-related data 25 are used in the eighth embodiment, these may be the pressing pressure detecting unit 13 and the stable fat thickness-related data 26.

The visceral fat calculating unit 24 may have a structure in which the calculating unit 7 is the same.

Ninth Embodiment

Figure 17:
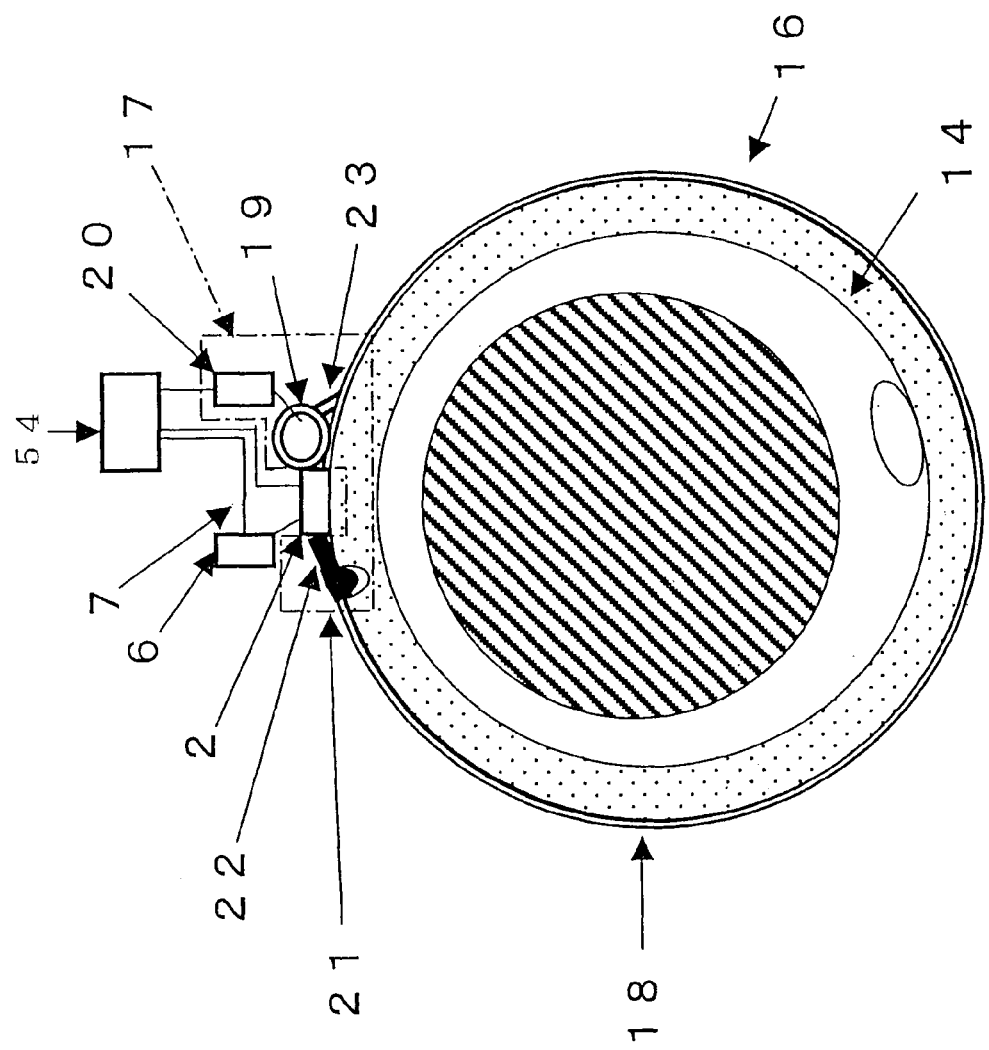
FIG. 17 is a structural view of a visceral fat measuring apparatus according to a ninth embodiment of the present invention.

FIG. 17 shows the structure of a visceral fat measuring apparatus according to a ninth embodiment of the present invention. Descriptions of parts similar to those of the eighth embodiment are omitted, and only different parts will be described.

The structure is different from that of the eighth embodiment in that a visceral fat calculating unit 54 is provided and that neither the calculating unit 7 nor the pressure/fat thickness-related data 25 is provided. Except these, the structure is similar to that of the eighth embodiment.

Next, the operation of the present embodiment will be described.

The abdominal girth measuring unit 17 of the visceral fat measuring apparatus according to the ninth embodiment measures the abdominal girth L in a similar manner to that of the eighth embodiment.

The abdominal girth measuring unit 17 transmits the measured abdominal girth L to the visceral fat calculating unit 54. The pressing pressure measuring unit 6 measures the pressing pressure, and transmits it to the visceral fat calculating unit 54. The subcutaneous fat measuring unit 2 measures the subcutaneous fat thickness, and transmits it to the visceral fat calculating unit 54.

The visceral fat calculating unit 54 obtains the amount S of visceral fat by use of the expression 5 described in the seventh embodiment with the pressing pressure being F, the subcutaneous fat thickness measured by the subcutaneous fat measuring unit 2 being T and the abdominal girth being L.

The structures other than these will not be described because they are similar to those of the eighth embodiment.

As described above, the visceral fat measuring apparatus according to the ninth embodiment is capable of accurately obtaining the abdominal girth L' excluding the subcutaneous fat thickness and the amount of visceral fat.

Tenth Embodiment

Figure 18:
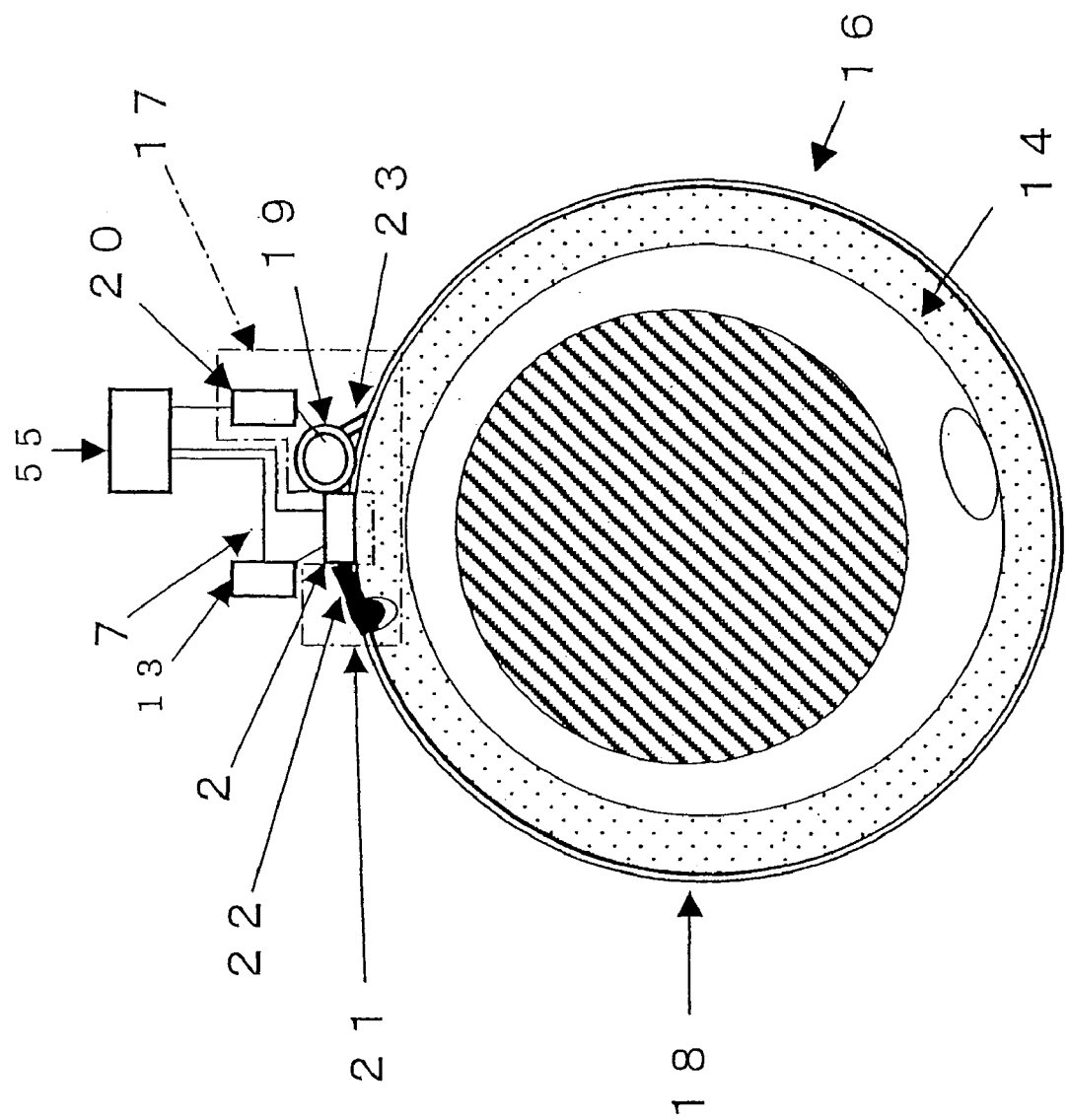
FIG. 18 is a structural view of a visceral fat measuring apparatus according to a tenth embodiment of the present invention.

FIG. 18 shows the structure of a visceral fat measuring apparatus according to a tenth embodiment of the present invention. Descriptions of parts similar to those of the eighth embodiment are omitted, and only different parts will be described.

The structure is different from that of the eighth embodiment in that a visceral fat calculating unit 55 is provided, that neither the calculating unit 7 nor the pressure/fat thickness-related data 25 is provided and that the pressing pressure detecting unit 13 is provided instead of the pressing pressure measuring unit 6.

Next, the operation of the present embodiment will be described.

The abdominal girth measuring unit 17 of the visceral fat measuring apparatus according to the tenth embodiment measures the abdominal girth L in a similar manner to that of the eighth embodiment. The abdominal girth measuring unit 17 transmits the measured abdominal girth L to the visceral fat calculating unit 55.

The subcutaneous fat measuring unit 2 of the visceral fat measuring apparatus according to the tenth embodiment measures the subcutaneous fat thickness in a similar manner to that of the third embodiment. That is, the subcutaneous fat measuring unit 2 measures the subcutaneous fat thickness in the condition where a pressing pressure of not less than the prescribed value is applied. Then, the subcutaneous fat measuring unit 2 transmits the measured subcutaneous fat thickness to the visceral fat calculating unit 55.

The visceral fat calculating unit 55 obtains the amount S of visceral fat by use of the expression 6 described in the seventh embodiment with the subcutaneous fat thickness measured by the subcutaneous fat measuring unit 2 in the condition where a pressing pressure of not less than the prescribed value is applied being $T_\infty$ and the abdominal girth being L.

The structures other than these will not be described because they are similar to those of the eighth embodiment.

As described above, the visceral fat measuring apparatus according to the tenth embodiment is capable of accurately obtaining the abdominal girth L' excluding the subcutaneous fat thickness and the visceral fat amount.

While the pressure/fat thickness-related data 25 or the stable fat thickness-related data 26 is provided separately from the calculating unit 7 in the embodiments, these databases may be included in the calculating unit 7.

Moreover, the body fat ratio can be calculated by the visceral fat measuring apparatus according to each of the embodiments, the subcutaneous fat thickness and the visceral fat amount obtained by the visceral fat measuring apparatus, the height, and the weight.

Moreover, the obtained subcutaneous fat thickness and visceral fat amount can be transmitted to an external apparatus by separately provided communication means.

The program of the present invention is a program of causing a computer to execute the functions of the above-described visceral fat measuring apparatus of the present invention and one or both of the calculating unit and the visceral fat calculating unit of the visceral fat measuring apparatus, said program operating in concert with the computer.

Moreover, the recording medium of the present invention is a recording medium holding all or part of a program or a database of causing a computer to execute the functions of the above-described visceral fat measuring apparatus of the present invention and the calculating unit or the visceral fat calculating unit of the visceral fat measuring apparatus, said recording medium being computer-readable and said program or said database that is read out being used in concert with the computer.

Moreover, a usage of the program of the present invention may be such that the program is recorded on a computer-readable recording medium and operates in concert with a computer.

Moreover, the recording medium includes ROMs, and the transmission medium includes: transmission media such as the Internet; light; radio waves; and sound waves.

Moreover, the above-mentioned computer of the present invention is not limited to pure hardware such as a CPU, but may include firmware, an OS, and peripherals.

As described above, the structure of the present invention may be implemented either via software or via hardware.

According to the present invention, a visceral fat measuring apparatus and a visceral fat measuring method can be provided that are excellent in measurement repeatability and capable of measuring the subcutaneous fat thickness in the condition where no pressure is applied to the measurement part.

According to another aspect of the invention, a visceral fat measuring apparatus and a visceral fat measuring method can be provided that are capable of measuring an information amount correlated with the visceral fat amount and not including the influence of the subcutaneous fat.

The invention claimed is:

1. A visceral fat measuring apparatus comprising:
a subcutaneous fat measuring unit having a contact face shaped to come into contact with a living body surface, and configured to measure a subcutaneous fat thickness with said contact face being pressed against said living body surface;
a pressing pressure measuring unit configured to monitor a pressure at which said contact face is pressed against the living body surface; and
a visceral fat calculating unit configured to calculate an amount of visceral fat by use of an Expression 2 based on the subcutaneous fat thickness measured by said pressing pressure measuring unit, and the pressure monitored by said pressing pressure measuring unit:

$$S=D\times((T-Be^{-CF})/(A-1)e^{-CF}+1)+E \qquad \text{(Expression 2)}$$

where S is the amount of visceral fat, F is the monitored pressure, T is the measured subcutaneous fat thickness, A, B, C, D and E are predetermined constants, and e is a base of a natural logarithm,
wherein said subcutaneous fat measuring unit is an optical subcutaneous fat measuring apparatus.

2. A visceral fat measuring apparatus comprising:
a subcutaneous fat measuring unit having a contact face shaped to come into contact with a living body surface, and configured to measure a subcutaneous fat thickness with said contact face being pressed against said living body surface;
a pressing pressure measuring unit configured to monitor a pressure at which said contact face is pressed against the living body surface; and
a visceral fat calculating unit configured to calculate an amount of visceral fat by use of an Expression 2 based on the subcutaneous fat thickness measured by said pressing pressure measuring unit, and the pressure monitored by said pressing pressure measuring unit:

$$S=D\times((T-Be^{-CF})/(A-1)e^{-CF}+1)+E \qquad \text{(Expression 2)}$$

where S is the amount of visceral fat, F is the monitored pressure, T is the measured subcutaneous fat thickness, A, B, C, D and E are predetermined constants, and e is a base of a natural logarithm,
wherein said subcutaneous fat measuring unit comprises:
an ultrasonic element configured to measure the subcutaneous fat thickness by use of a reflected wave;
a domical lid to form an enclosed space between said ultrasonic element and said living body surface; and
a soft body of being filled in the space.

3. A visceral fat measuring apparatus comprising:
a subcutaneous fat measuring unit having a contact face shaped to come into contact with a living body surface, and configured to measure a subcutaneous fat thickness with said contact face being pressed against said living body surface;
a pressing pressure measuring unit configured to monitor a pressure at which said contact face is pressed against the living body surface; and
a visceral fat calculating unit having an abdominal girth inputting unit configured to input an abdominal girth, said visceral fat calculating unit being configured to calculate an amount of visceral fat by use of an Expression 5 based on the measured subcutaneous fat thickness, the monitored pressure, and the input abdominal girth:

$$S=G\times L-H\times((T-Be^{-CF})/(A-1)e^{-CF}+1)+I \qquad \text{(Expression 5)}$$

where S is said amount of visceral fat, F is the monitored pressure, T is the measured subcutaneous fat thickness, L is the abdominal girth, A, B, C, D, E, G, H and I are predetermined constants, and e is a base of a natural logarithm, wherein said abdominal girth measuring unit comprises:

a string;

a reel of winding up said string; and a counter of counting the number of rotations of said reel.

4. The visceral fat measuring apparatus according to claim 3, wherein said abdominal girth calculating unit comprises a tension adjusting mechanism configured to hold a tension of said string at a predetermined value.

5. A visceral fat measuring apparatus comprising:

a subcutaneous fat measuring unit having a contact face shaped to come into contact with a living body surface, and configured to measure a first subcutaneous fat thickness with said contact face being pressed against said living body surface;

a calculating unit configured to calculate, based on said first subcutaneous fat thickness, a second subcutaneous fat thickness expected in the absence of the pressure being applied to the living body surface;

a visceral fat calculating unit configured to calculate an amount of visceral fat from said second subcutaneous fat thickness; and a database configured to store a relationship which defines a correlation between a plurality of the first subcutaneous fat thicknesses and a plurality of said second subcutaneous fat thicknesses with regard to a predetermined pressure at which said contact face is pressed against said living body, said calculating unit being configured to refer to said database for retrieving therefrom said second subcutaneous fat thickness corresponding to said first subcutaneous fat thickness measured by said subcutaneous fat measuring unit when said contact face is pressed against said living body at said predetermined pressure, wherein said predetermined pressure is 10000 Pa or more, wherein said subcutaneous fat measuring unit is an optical subcutaneous fat measuring apparatus.

6. A visceral fat measuring apparatus comprising:

a subcutaneous fat measuring unit having a contact face shaped to come into contact with a living body surface, and configured to measure a first subcutaneous fat thickness with said contact face being pressed against said living body surface;

a calculating unit configured to calculate, based on said first subcutaneous fat thickness, a second subcutaneous fat thickness expected in the absence of the pressure being applied to the living body surface; and a visceral fat calculating unit configured to calculate an amount of visceral fat from said second subcutaneous fat thickness, wherein said subcutaneous fat measuring unit is an optical subcutaneous fat measuring apparatus, wherein:

said subcutaneous fat measuring unit comprises an LED and a photo diode;

said LED and said photo diode are respectively disposed on said contact surface;

said LED is configured to emit light to the living body surface, whereby diffused and attenuated light appears on the living body surface;

said photo diode is configured to measure the diffused and attenuated light; and said subcutaneous fat measuring unit is configured to measure the first subcutaneous fat thickness in terms of the diffused and attenuated light which is detected by the photo diode.

7. A visceral fat measuring apparatus comprising:

a subcutaneous fat measuring unit having a contact face shaped to come into contact with a living body surface, and configured to measure a first subcutaneous fat thickness with said contact face being pressed against said living body surface;

a calculating unit configured to calculate, based on said first subcutaneous fat thickness, a second subcutaneous fat thickness expected in the absence of the pressure being applied to the living body surface; and a visceral fat calculating unit configured to calculate an amount of visceral fat from said second subcutaneous fat thickness, wherein said subcutaneous fat measuring unit comprises:

an ultrasonic element configured to measure the subcutaneous fat thickness by use of a reflected wave;

a domical lid configured to form an enclosed space between said ultrasonic element and said living body surface; and a soft body of being filled in the space, wherein:

said ultrasonic element is disposed on said contact surface;

said ultrasonic element being configured to emit an ultrasonic wave to the living body surface; said ultrasonic wave being reflected by the living body tissue, whereby the reflected wave is generated;

said ultrasonic element being configured to observe the reflected wave; and said ultrasonic element configured to measure said first subcutaneous fat thickness by use of the reflected wave.

8. A visceral fat measuring apparatus according to claim 1, wherein said subcutaneous fat measuring unit comprising an LED and a photo diode, said LED and said photo diode are respectively disposed on said contact surface, said LED being configured to emit light to the living body surface, whereby diffused and attenuated light is appeared on the living body surface, said photo diode being configured to measure the diffused and attenuated light, and said subcutaneous fat measuring unit being configured to measure the first subcutaneous fat thickness in terms of the diffused and attenuated light which is detected by the photo diode.

9. The visceral fat measuring apparatus according to claim 5, wherein said subcutaneous fat measuring unit comprising an LED and a photo diode, said LED and said photo diode are respectively disposed on said contact surface, said LED being configured to emit light to the living body surface, whereby diffused and attenuated light is appeared on the living body surface, said photo diode being configured to measure the diffused and attenuated light, and said subcutaneous fat measuring unit being configured to measure the first subcutaneous fat thickness in terms of the diffused and attenuated light which is detected by the photo diode.

10. The visceral fat measuring apparatus according to claim 2, wherein said ultrasonic element is disposed on said contact surface, said ultrasonic element being configured to emit an ultrasonic wave to the living body surface, said ultrasonic wave being reflected by the living body tissue, whereby the reflected wave is generated, said ultrasonic element being configured to observe the reflected wave, and said ultrasonic element configured to measure said first subcutaneous fat thickness by use of the reflected wave.

* * * * *